(12) United States Patent
Peltola et al.

(10) Patent No.: US 10,639,501 B2
(45) Date of Patent: May 5, 2020

(54) CREATING TREATMENT FIELD USING INITIAL FIELD AND PATIENT SPECIFIC GEOMETRY AND ACHIEVABLE DOSE

(71) Applicant: Varian Medical Systems International AG, Cham (CH)

(72) Inventors: Jarkko Peltola, Tuusula (FI); Janne Nord, Espoo (FI); Santtu Ollila, Helsinki (FI); Mikko Vainio, Espoo (FI); Esa Kuusela, Espoo (FI)

(73) Assignee: Varian Medical Systems International AG, Cham (CH)

( * ) Notice: Subject to any disclaimer, the term of this patent is extended or adjusted under 35 U.S.C. 154(b) by 366 days.

(21) Appl. No.: 15/703,604

(22) Filed: Sep. 13, 2017

(65) Prior Publication Data

US 2018/0085596 A1 Mar. 29, 2018

Related U.S. Application Data

(60) Provisional application No. 62/399,270, filed on Sep. 23, 2016.

(51) Int. Cl.
*A61N 5/10* (2006.01)
*G21K 1/02* (2006.01)

(52) U.S. Cl.
CPC .......... *A61N 5/103* (2013.01); *A61N 5/1081* (2013.01); *A61N 5/1045* (2013.01); *A61N 5/1047* (2013.01); *A61N 2005/1041* (2013.01); *G21K 1/02* (2013.01)

(58) Field of Classification Search
CPC .... A61N 5/103; A61N 5/1081; A61N 5/1045; A61N 5/1047; A61N 2005/1041; G21K 1/02
USPC .......................................................... 378/65
See application file for complete search history.

(56) References Cited

U.S. PATENT DOCUMENTS

2011/0153547 A1  6/2011  McNutt et al.

FOREIGN PATENT DOCUMENTS

| WO | 2011042819 | 4/2011 |
| WO | 2015044924 | 4/2015 |
| WO | 2016088075 | 6/2016 |
| WO | 2018054873 | 3/2018 |

OTHER PUBLICATIONS

International Application No. PCT/EP2017/073568, "International Search Report and Written Opinion", dated Mar. 23, 2018, 17 pages.
International Application No. PCT/EP2017/073568, "Invitation to Pay Add'l Fees and Partial Search Report", dated Jan. 4, 2018, 6 pages.

*Primary Examiner* — Courtney D Thomas
(74) *Attorney, Agent, or Firm* — Kilpatrick Townsend & Stockton LLP

(57) ABSTRACT

Methods and systems are provided for developing radiation therapy treatment plans. A treatment template with radiation fields can be chosen for a patient based on a tumor location. Static radiation field positions can be adjusted for the patient, while arc radiation fields may remain the same. Static radiation field positions can be adjusted using dose gradient, historical patient data, and other techniques.

20 Claims, 12 Drawing Sheets

CREATING TREATMENT FIELD USING INITIAL FIELD AND PATIENT SPECIFIC GEOMETRY AND ACHIEVABLE DOSE

CROSS-REFERENCES TO RELATED APPLICATIONS

The present application is a non-provisional application of and claims the benefit and priority under 35 U.S.C. 119(e) of U.S. Provisional Application No. 62/399,270, filed Sep. 23, 2016 entitled "CREATING TREATMENT FIELD USING INITIAL FIELD AND PATIENT SPECIFIC GEOMETRY AND ACHIEVABLE DOSE," the entire contents of which is incorporated herein by reference for all purposes.

FIELD

The present disclosure generally relates to treatment planning for a tumor, and more particularly to determining a radiation field setup based on an initial field template and patient-specific information.

BACKGROUND

In radiation therapy, there is a need for tools for that can automatically generate treatment plans with optimum radiation field positions (e.g., angles from which to provide radiation). Currently, the best possible treatment plan for a patient is generated by manually trying different field position setups and performing full dose optimization for each attempted field setup. This is very time-consuming, and the success of the process depends on the operator's capabilities.

Further, automatic processes for generating field setups often produce geometrically different field setups, even when two patient cases are similar. Such variation can reduce an operator's familiarity with optimized treatment plans and can reduce confidence that a treatment plan is safe and viable.

Therefore, it is desirable to provide techniques for addressing these problems.

BRIEF SUMMARY

Embodiments of the present invention provide systems, methods, and apparatuses for determining radiation treatment plan field setups with trustworthy and personalized radiation fields. A template with proven fields can be chosen based on the size, location, and shape of a tumor, as well as patient geometry (e.g., patient body shape and organ locations). The template can include one or more arc fields and one or more static fields. The arc fields can be used as shown in the template. The static field positions can be adjusted based on the specific facts of the case (e.g., information about the tumor, patient, dose gradient, etc.). The static fields may be constrained to a region (e.g., volume or surface) defined in the template. As a result, proven fields are utilized, but can be personalized for a patient.

Other embodiments are directed to systems and computer readable media associated with methods described herein.

A better understanding of the nature and advantages of embodiments of the present invention may be gained with reference to the following detailed description and the accompanying drawings.

DEFINITIONS

Figure 1:
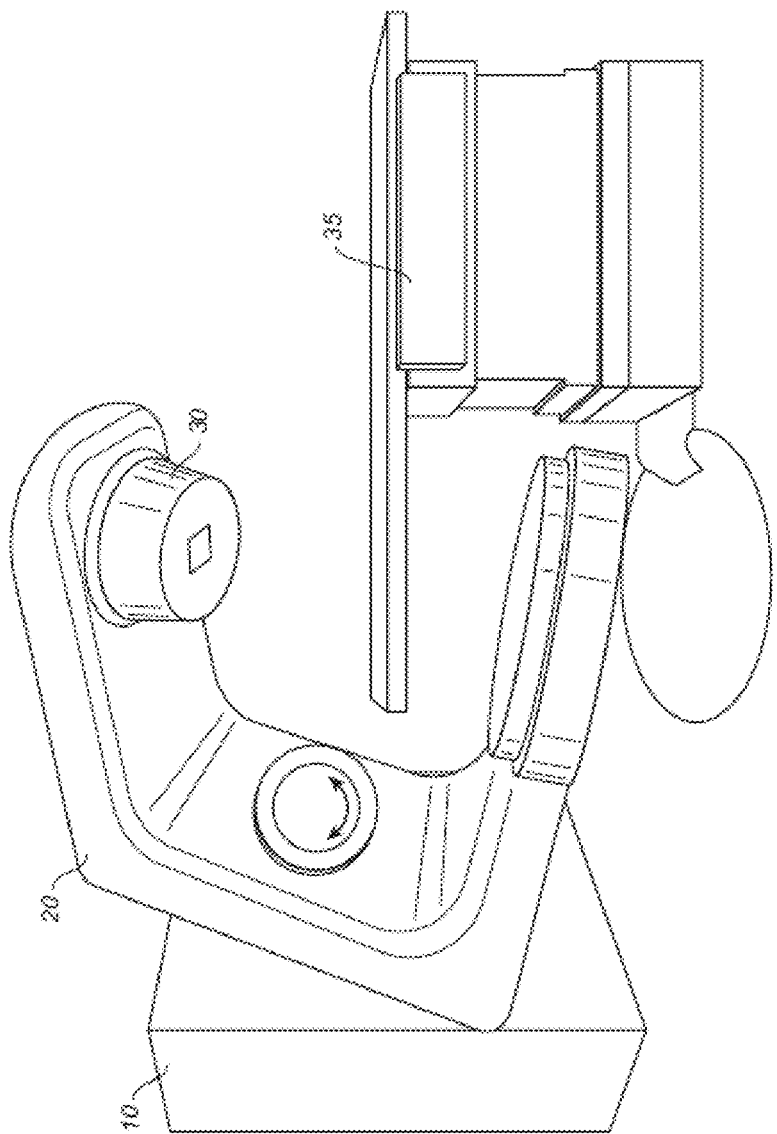
FIG. 1 is a perspective view of a radiation treatment system.

"Radiation" refers to any particles (e.g., photons, electrons, protons etc.) used to treat tissue, e.g., tumors. Examples of radiation include high energy x-rays, gamma rays, electron beams, and proton beams. The different particles can correspond to different types (strategies) of radiation treatments. Other treatment types can include chemotherapy and surgery. The "treatment volume" refers to the entire volume that will be subjected to radiation, and is sometimes referred to as the "irradiated volume." The "target structure", "target volume", and "planning target volume" ("PTV") refer to tissue intended to receive a therapeutic prescribed dose.

A "treatment plan" can include information about strategy and actions for treating a patient ailment. A treatment plan can include a dose distribution, machine parameters for achieving the dose distribution for a given patient, and information about the given patient. Machine parameters can include angles (or fields) from which to radiate a patient treatment area, a dose to apply from each field, beam collimation settings, and any other suitable parameters.

A "dose distribution" provides information about the variation in the dose of radiation with position. A dose distribution can take many forms, e.g., a dose volume histogram (DVH) or a dose matrix. A DVH can summarize three-dimensional (3D) dose distributions in a graphical 2D format, e.g., where the horizontal axis is the dose (e.g., in units of grays—Gy) absorbed by the target structure (e.g., a tumor) and the horizontal axis is the volume percentage. In a differential DVH, the height of a bar at a particular dose indicates the volume of the target structure receiving the particular dose. In a cumulative DVH, the height of a bar at a particular dose represents the volume of the structure receiving greater than or equal to that dose. The cumulative DVH is generally a curve (e.g., when small bin sizes are used), whereas the differential DVH is generally a disjoint bar graph. A drawback of a DVH is that it offers no spatial information; i.e., a DVH does not show where within a structure a dose is received. A dose matrix can provide the dose that each part of the body receives.

A "dose prediction model" receives patient data and outputs a dose distribution that is predicted to be obtainable. Different types of radiation treatments can have different models. The patient data can include diagnostic information (e.g., general tumor location or stage information) and geometric information (e.g., the spatial geometry of the tumor and of other organs in the patient). A dose prediction model can predict a dose distribution for a given field setup and a given target dose (e.g., a dose prescription of a certain amount of Gy). A particular model can have an accuracy (reliability) associated with the predicted dose distribution. The accuracy can be determined from a set of test treatment plans whose dose distribution has been determined via other means (e.g., by optimizing a cost function). For example, the accuracy can be determined based on how well the model predicts the actual dose distributions obtained by optimizing a cost function.

A "dose gradient" can describe how a dose distribution changes based on one or more parameters. For example, a dose gradient can include a rate of dose distribution change as a function of one or more dose delivery parameters. Accordingly, a dose gradient can provide information about the dose that may be received at a certain point (or within a certain volume) for a given set of radiation parameters. The dose gradient can be dependent on the radiation angle, characteristics of the radiation beam, and the radiation intensity, and any other suitable parameter that can affect the dose received in a certain area. For example, the parameters that affect dose gradient can include MLC leaf positions, radiation fluence, parameters defining a radiation field position (e.g., gantry angle, collimator angle, treatment table angle), and any other suitable parameter.

A "spatial gradient" refers to a rate at which dose changes with location. For example, a spatial gradient can provide the rate at which the dose absorbed in tissue decreases with distance from the center of a radiation beam (e.g., in a direction perpendicular to the surface of a radiation target, or perpendicular to the beam direction). Due to scattering, a radiation beam may spread and scatter outward from the beam path within the patient. As a result, some dose may be applied to tissue outside of the intended beam pathway. More dose may be applied to closer tissue, and the dose may taper with distance from the beam. This tapering affect can be described by the spatial gradient. A dose may taper exponentially, linearly, or in any other suitable fashion. The dose can continually spread with depth, as the beam may continue to scatter. In some embodiments, the dosage may also decrease with depth (e.g., due to radiation absorption). A spatial gradient may be used to describe how the dose decreases with depth.

An "isocenter" may be a point around which a radiation treatment revolves. For example, a gantry and collimator may rotate with respect to an isocenter of a treatment area while providing radiation. An isocenter may be a spatial center of a tumor, a tumor center-of-mass, or any other suitable point to orient radiation toward.

The term "optimal" refers to any value that is determined to be numerically better than one or more other values. For example, an optimal value is not necessarily the best possible value, but may simply satisfy a criterion (e.g. a change in a cost function from a previous value is within tolerance). Thus, the optimal solution can be one that is not the very best possible solution, but simply one that is better than another solution according to a criterion.

DETAILED DESCRIPTION

A radiation treatment plan typically includes instructions for controlling a radiation treatment system, such that the radiation treatment system can provide radiation to a patient in a specified manner. Radiation may be provided from a fixed point (as in a static radiation field), or radiation can be provided while the radiation source (e.g., a collimator on a gantry) is moved along a certain pathway (as in an arc radiation field). Optimum radiation field setups (e.g., geometrical positions from which radiation is provided) can depend on the patient geometry (e.g., patient size, shape, and internal organ locations), the size and location of a tumor target area, the estimated dose, and other suitable factors.

Embodiments of the invention provide methods and systems for identifying optimized radiation field setups. In some embodiments, a template can be generated for a certain type of tumor or treatment. The template can include one or more arc fields (at one or more arc field pathways) and one or more static fields (at one or more static field positions). The static field positions can be adjusted for a specific patient. However, the static field positions may be constrained within a certain region (e.g., within a certain volume, within a certain set of coordinates on a two-dimensional surface, within a certain range of collimator vectors, etc.). The static field positions can be optimized using an estimated dose and dose gradient, using geometrical information, and/or using historical patient data. As a result, a treatment plan can be generated for a specific patient that uses a trusted template, yet allows the template to be fine-tuned for the specific patient.

Embodiments of the invention also allow a treatment plan or template to be used for a second target area and isocenter. For example, a treatment plan for a first target area can be transformed (e.g., the arc fields and static fields can be transformed) for use at a second target area. A transformation (e.g., translation, rotation, or scaling) that moves the first isocenter to the second isocenter can be used to transform the treatment plan.

I. Introduction

A. Radiation Systems

Figure 2:
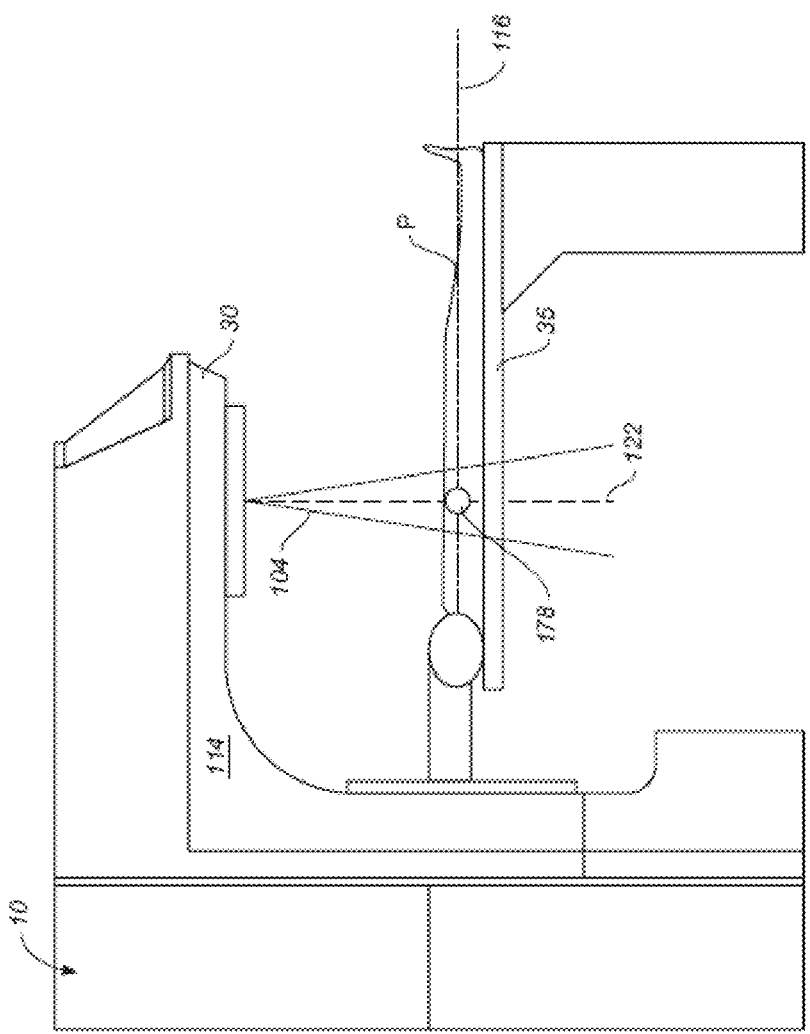
FIG. 2 is a side view of a radiation treatment system.

FIGS. 1 and 2 depict a radiation treatment system of the type which may be used in connection with the present invention. Referring to FIG. 1, a perspective view of radiation treatment system (in this case a linear accelerator) is shown. Typically, such a system is capable of generating either an electron (particle) beam or an x-ray (photon) beam for use in the radiotherapy treatment of patients on a treatment table 35. Other radiation treatment systems are capable of generating heavy ion particles such as protons. For purposes of the present discussion, only x-ray irradiation will be discussed. However, it will be appreciated by those skilled in the art that the same principles apply to other systems.

Stand 10 supports a rotatable gantry 20 with a treatment head 30. Next to stand 10 there is arranged a control unit (not shown) which includes operational electronics for controlling the different modes of operation of the accelerator. A high voltage source is provided within the stand or in the gantry, to supply voltage to an electron gun (not shown) positioned on an accelerator guide located in gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

Referring now to FIG. 2, a somewhat more detailed side view of a radiation treatment system of the type which may be used in connection with the present invention is shown. A patient P is shown lying on treatment table 35. X-rays formed as described above are emitted from the target in treatment head 30 in a divergent beam 104. Typically, a patient plane 116, which is perpendicular to the page in FIG. 2, is positioned about one meter from the x-ray source or target, and the axis of gantry 20 is located on plane 116, such that the distance between the target and isocenter 178 remains constant when gantry 20 is rotated. Isocenter 178 is at the intersection between patient plane 116 and the central axis of beam 122. A treatment volume to be irradiated is located about the isocenter.

"Jaws" (not shown) or x-ray collimators comprising an x-ray blocking material, are positioned in head 30 to define the width of the x-ray beam at the patient plane. Typically, the jaws are moveable and, when fully open, define a maximum beam of about 40 cm×40 cm at patient plane 116. A multileaf collimator ("MLC") (not shown in FIG. 2) is positioned at the exit of head 30, to further shape the x-ray beam. Since its introduction in 1990 the MLC has become a standard feature of most radiation treatment systems. Current MLCs sold by the assignee of the present invention use up to 120 individually controllable leaves, typically thin slices of tungsten, that can be moved into or out of the x-ray beam under the control of system software. The MLC can be used to collimate the x-rays to provide conformal treatment of tumors from various angles ("3D conformal,") as well as intensity modulated radiotherapy ("IMRT"), whereby different radiation doses are delivered to different portions of the treatment area. The treatment volume, i.e., the irradiated volume proximate to the isocenter in the path of the x-ray beam, is defined by the jaws, the angle of the head and the MLC. In IMRT the leaves of the MLC are moved, such that the treatment volume comprises the total volume exposed during the course of a treatment. In arc therapy, the gantry is moved while radiation is delivered.

B. Plan Generation

Modern radiation therapy techniques involve the use of a treatment plan designed to irradiate a desired target volume, usually corresponding to a tumor, with a desired dose of x-rays (or other radiation). Most treatment planning involves the use of the MLC to provide conformal and/or intensity modulated irradiation. Generally speaking, a treatment plan comprises irradiating one or more selected portions of the treatment volume with a calculated dose of x-rays.

As noted above, an important aspect of the conformal and IMRT techniques that are associated with the use of MLCs is the ability to both provide a homogenous desired dose of radiation to a target volume while minimizing the dose delivered to adjacent healthy tissue. A dose of radiation can be delivered to adjacent healthy tissue even if the healthy tissue is not directly in the intended path of the radiation. For example, beam scattering can cause radiation to bleed over onto healthy tissue. This dose spillage can damage adjacent healthy tissue. Accordingly, this dose spillage is considered when generating a treatment plan.

Dose spillage can be influenced by several factors. For example, dose spillage can have strong correlation to the given field geometry (e.g., the chosen directions for incoming radiation).

Due to dose spillage, a radiation beam typically does not have an abrupt edge. Instead, the radiation intensity gradually tapers with distance from the beam's centerline. The rate of radiation fall-off with distance from the beam's centerline can be described by a spatial gradient.

In addition to this dose spillage, delivering radiation to a target area often requires sending radiation through one or more organs at risk (OARs). For example, an OAR may lie partially in the path of the radiation beam (e.g., in between the radiation field position and the target area).

When there is only a small number of radiation field positions being used (e.g., 1-10 fields), the geometry of the fields can have significant influence on how much radiation dose the OAR receives. For example, in a setup with five fields, each field may provide a significant portion of the total dose. As a result, each of the radiation fields has the potential to cause considerable harm to an OAR if placed in an undesirable position (e.g., a position that irradiates an OAR more than necessary).

The quality of a treatment plan can be evaluated based on the dose quality of the treatment plan. For example, the dose quality can describe the amount of radiation applied to healthy tissue, and the amount of radiation applied to certain sensitive organs. A treatment plan will have a higher dose quality if the entire treatment area receives the entire dose and the surrounding healthy tissue receives only a small dose (e.g., a certain OAR may safely receive 1% or less of the total dose). Healthy tissue can be protected by distributing the dose around different areas of surrounding healthy tissue, such that no local region is over-exposed.

As mentioned above, a treatment plan can include specifications for a number of radiation delivery parameters. For example, the shape of the radiation beam can be controlled (e.g., by adjusting the leaves of the MLC), the position and angle of the radiation field can be specified (e.g., via positions for the rotatable gantry, treatment table, and treatment head), and the duration and intensity of the radiation can be indicated. The next section describes different options for radiation beam angles.

C. Static Fields

A static field is a radiation field that is provided from the same location throughout the irradiation. For example, the radiation source (e.g., a beam collimator) can be set to a certain position relative to the patient's body. A static field position can include both a distance (e.g., distance from an isocenter) and an angle (e.g., an incoming direction of beam approach from the perspective of the isocenter). Accordingly, a static field may be associated with certain settings for the gantry, treatment table, and/or treatment head (which may remain fixed while a static field is delivered). Static fields may be aimed directly at the isocenter of the treatment area, or may be centered on a point different than the isocenter.

A specific dose can be assigned to the static field. After the dose is provided, a second dose may be provided for a different static field at a different static field position. For example, in a treatment plan that utilizes multiple static fields, a radiation beam can be turned off after a first static field is applied. Then, the radiation system settings can be changed for a second static field, and the radiation beam can be turned on again for the second static field. The total desired dose can be divided among the different static fields (e.g., equally or unequally). In some embodiments, intensity-modulated radiation therapy (IMRT) can utilize static fields.

In some embodiments, a static field may include one fixed radiation beam shape that provides conformal radiation. For example there may be one set of fixed MLC leaf settings and/or collimator settings. Alternatively, the beam shape and/or radiation intensity (e.g., fluence) can vary during throughout the time of static field radiation. The MLC leaves, collimator settings, and radiation intensity may shift in a predefined manner during irradiation, providing.

D. Arc Fields

An arc field is a radiation field that is provided from the different locations throughout the irradiation. For example, the radiation source (e.g., a beam collimator) have a varying position relative to the patient's body. In some embodiments, an arc field may allow every parameter to change. For example, the arc field may include a varying distance, a varying angle, a varying beam shape, varying radiation intensity, and/or any other type of changing parameter. An arc field may include a starting position (e.g., a starting angle and distance), an ending position (e.g., an ending angle and distance), and any suitable information about the pathway taken between the starting and ending positions (e.g., a set of intermediary positions through which to move). Accordingly, an arc field may be associated with gantry rotation information, gantry speed information, radiation intensity settings, treatment head settings, and MLC leaf and collimator settings.

While providing an arc field, the gantry and treatment table may move so that the radiation source rotates relative to the patient. As a result, the angle of incidence to the patient changes while the beam moves along an arc field pathway. The rotation speed, intensity, and beam shape can be controlled such that desired radiation doses reach selected portions of the treatment volume from certain angles. An arc field may aim directly at the isocenter throughout the entire dose delivery, or the beam may be centered on a different area at certain times.

In some embodiments, an arc field may only curve within a two dimensional plane. Alternatively, an arc field can take any suitable course. Further, an arc field pathway may start at a zero degree angle (e.g., the treatment head may be level with the patient) and travel over the patient to the other side at a 180 degree angle. Alternatively, the arc field may cover any other suitable range of angles. In some embodiments, an arc field may not drop below zero degrees so that the beam is not blocked by the treatment table. In other embodiments, an arc field can cover an entire 360 degree range around a patient.

As an example, arc fields can be used in volumetric arc therapy (VMAT). VMAT can be a specific form of IMRT.

Arc fields can allow radiation to be delivered to a treatment area while the radiation beam moves across a range of incident angles. As a result, a full dose can be delivered to the tumor while limiting overexposure to specific regions of intermediary healthy tissue. Instead of sending all radiation through the same portion of healthy tissue, the dose is dispersed across different sections of healthy tissue.

As mentioned above, in more complex plans, the MLC leaves can be moved into different positions between or during irradiations. The leaves of the MLC can either be moved iteratively into different positions while the beam is off, with irradiation between movements, (such that the leaves are static during irradiation), or they can be continually moved during irradiation in a "sliding window" or other variable aperture technique.

Arc fields and static fields may have different properties. For example, it may be easy to understand how an arc field contributes to a treatment, as an arc field may simple rotate around the treatment table. This simple rotation may provide a specified dose to the target area (e.g., a rounded dose applied uniformly to the treatment area), and a small diluted dose to intervening healthy tissue. A static field, on the other hand, may have properties that are not immediately clear. For example, a static field may have any field position (e.g., an combination of gantry, treatment bed, and collimator settings), and it may not be obvious if that position will have negative side-effects or collimation issues. Additionally, a combination of static fields may produce a non-uniform dose (e.g., a star-shaped dose), as different static fields may overlap and combine in specific areas.

E. Challenges with Generating Plans

Due to the complexity of human anatomy, as well as varying types, locations, and shapes of tumors, the specific facts of patient cases can vary widely. Accordingly, there may be unique geometries, differing areas of sensitive healthy tissue, specific beam scattering conditions, and other special considerations when developing a treatment plan for a new patient. Thus, generating a treatment plan is often a complex procedure, and patients typically need specialized treatment plans.

It can be difficult to determine what types of strategies to use in a treatment plan. For example, a treatment plan can include static fields, arc fields, different doses, different collimator and MLC leaf settings, etc. Some plans can include both static fields and arc fields that expose the treatment area differently. For example, in arc treatments, the plane of gantry rotation can heavily influence the achievable spatial gradients between target and an OAR (organ at risk). This may sometimes be compensated by adding static fields from different radiation angles in respect to the target. However, not all angles can be used because of the treatment table collision issues. Thus, it can be difficult to tell beforehand if the angle is clinically viable and mechanically acceptable.

It is difficult to know what static fields can be added to improve the plan quality. With an arc field already providing some dose to the treatment area and some dose to healthy tissues, it is not obvious what static fields can add the correct complementary dose to the treatment area without overdosing different areas of healthy tissue. Additionally, it is complex to determine how to divide the dosage between arc fields and static fields.

As explained in more detail below, some techniques for optimizing the field geometry require too much manual manipulation as well as trial and error. These techniques can be imprecise, may not obtain true optimization, and can require too much time to be widely implemented. Other techniques can optimize one type of field, but in the process may provide a field geometry that is unfamiliar to a technician or doctor, who is likely to be suspicious and hesitant to use the new plan.

II. Optimization Techniques

There are several techniques for creating treatment plans for IMRT or conformal radiation therapy. Generally, these techniques are directed to solving the "inverse" problem of determining the optimal combination of angles, radiation doses and MLC leaf movements to deliver the desired total radiation dose to the target while minimizing irradiation of healthy tissue. This inverse problem is even more complex for developing arc therapy plans where the gantry is in motion while irradiating the target volume. Radiation oncologists or other medical professionals, such as medical physicists and dosimetrists, can use one of the available algorithms to develop and optimize a treatment plan. Such planning may start with volumetric information about the target tumor and about any nearby tissue structures. For example, such information may comprise a map of the planning target volume ("PTV"), such as a prostate tumor, which is prescribed by the physician to receive a certain therapeutic radiation dose with allowable tolerances. Volumetric information about nearby tissues may include for example, maps of the patient's bladder, spinal cord and rectum, each of which may be deemed an organ at risk that can only receive a much lower, maximum prescribed amount of radiation without risk of damage. This volumetric information along with the prescribed dose limits and similar objectives set by the medical professionals is the basis for calculating an optimized dose distribution and the treatment plan to deliver it. The volumetric information may, for example, be reduced to an objective function or a single figure of merit that accounts for the relative importance of various trade-offs inherent in such a plan, along with constraints that must be met for the plan to be medically acceptable or physically possible. Treatment planning algorithms can account for the capabilities of the specific radiation treatment system they are used with. For example, the type, energy level and fluence of the radiation beam, and the capabilities of the MLC.

A. Iterative Calculations and Manual Processes

Some treatment planning algorithms proceed by calculating the radiation dose received by each voxel in the treatment volume, adjusting one or more variable system parameters, such as the angle of irradiation or the positions of the MLC leaves, and then recalculating the dose received by each voxel. This process is ideally performed iteratively until an optimized plan is reached. However, the amount of time needed to perform the large number of calculations for each iteration places a practical limit on the number of iterations that can be performed. Accordingly, the algorithm is terminated after a predetermined amount of time, after a predetermined number of iterations, or after some other practical limit is reached. Generally speaking, there is a trade-off between the accuracy and speed of the different algorithms available for treatment planning.

These treatment planning algorithms are typically part of a manual treatment development process. For example, in addition to an algorithm that attempts to find the best angles and MLC positions, multiple types of user input and estimation may be involved, as well as testing multiple treatment options (e.g., trial and error for finding the best plan).

Typically, treatment plans use either arc fields or static fields. However, if both static fields and arc fields are used in the same treatment plan, each set of fields is optimized separately. A user (e.g., a dosimetrist or physician) may first determine a set of arc fields, and then determine a set of static fields.

As an example, a physician can provide some kind of prescription and requirements for the plan, e.g., must save the parotid gland or spine, and the target or the cancerous tissue requires at least sixty Gy (unit of radiation). A dosimetrist or physicist then spends several hours to create the treatment plan for a patient.

The user (e.g., dosimetrist) may, for a given patient, manually select one or more arc fields to test for a patient. For example, the user may choose angles of radiation that appear to best expose a treatment area and least expose sensitive healthy tissue (e.g., based on the location of the tumor, locations of nearby healthy tissue, other healthy tissue that may block certain incoming angles, etc.). The user may manually place starting and ending angles for the arc field, specify intermediary angles along the pathway, or otherwise provide information that specifies an arc field pathway. The user may also provide information about blocks to prevent radiation from hitting critical organs from certain directions. As a result, the user may have input information about arc fields, as well as information about the patient and tumor. These arc fields can then be tested in the following steps.

The user may then use optimization algorithms. An optimization algorithm may attempt to optimize radiation parameters that affect beam shape and fluence (e.g., MLC leaf settings and other machine parameters) and produce a treatment plan. Optimization objectives can guide the optimization algorithms. Typically, the field positions are not changed during this optimization process.

Optimization objectives can include, for example, providing the least damage possible to a specific OAR (e.g., no more than X Gy), at least a certain minimum total dose to the treatment area (e.g., at least Y Gy to at least 98% of the target volume), achieving a specific dose distribution, or any other suitable objective for dose delivery and patient outcome. Optimization objectives can be used to manually guide the optimization process so that it finds a way to produce a dose distribution that is clinically viable according to clinical objectives that a doctor has in mind.

After optimization, a dose can then be calculated. For example, the dosage can depend on the field positions, the patient geometry, and the optimized beam settings.

After all this work of choosing an arc field, optimizing the beam parameters, and determining dosage for the treatment plan, the dosimetrist or physician can review the treatment plan for quality. For example, a dose volume histogram can be determined and compared against optimization objectives. The physician may find that the dose distribution of the radiation treatment plan doesn't fill all of the requirements (or the critical requirements) that the physicians has specified. As a result, the physician may decide that the treatment plan is inadequate, so it should be changed or a new plan generated. In this case, the user may return to the beginning of the process, select different arc field pathways, and re-optimize the treatment plan. New plans can be compared to previous plans, potentially identifying meaningful variables to further refine. This trial and error process can continue until a medically viable plan is generated.

If desired, this process may also be executed for static fields. For example, the user may suspect that static fields have potential for improving the treatment. Accordingly, the user may select one or more potential static field positions. The beam parameters can be optimized for the given static field positions, a dosage may be calculated for the static fields, and the quality of the static field treatment plan can be evaluated (separate from the evaluation of any arc fields).

The total desired dosage for the tumor can be divided between the static fields and arc fields. The user may decide how the dosage should be divided, and then manually enter information about the desired dose for each set of fields. Also, after the different fields and corresponding doses are determined, the dose distributions for the different types of fields are added to obtain the total dose distribution.

This manual and iterative process presents a number of problems. For example, extensive user input is involved, such that the process involves much human labor and requires time. As mentioned, the user may need to provide positioning for arc fields and static fields, determine a total desired dosage, divide the dosage between the static fields and arc fields, etc. Further, the iterative nature of a trial-and-error process requires much time. Due to the human efforts and time needed, these processes are often not used, or if they are, the process is shortened so that the treatment plan is not fully optimized.

B. Unfamiliar Fields

Other processes for developing treatment plans can provide unfamiliar results, which may be untrusted by physicians and dosimetrists. For example, a user may create a starting set of incoming radiation angles for a certain type of treatment. A tumor next to the liver, for instance, may generally be exposed by radiation from a certain set of directions (e.g., from directly above the patient, at a 45 degree angle from the right, or any other suitable angle). These starting angles may not necessarily be specific static fields or arc fields, but may instead highlight regions and general areas that are a good starting point when searching for optimal fields for a specific patient. The starting angles may trace a suggested pathway for an arc field.

Having set the starting angles, the user may then input specific information about the patient. For example, the user may provide information about the size and location of the tumor, the patient's body shape and internal tissue layout, the desired dose for the tumor, optimization objectives (e.g., provide less than a certain dose to a certain OAR, provide less than a certain total dose to the patient, provide at least a certain dose to the treatment area, achieve a certain recovery time, or avoid certain side effects), and any other suitable information.

Based on the input information, an algorithm (e.g., a computer software tool) may be able to determine a treatment plan with suitable radiation field trajectories. The algorithm may provide one or more arc fields, one or more static fields, and/or any other suitable trajectory. There may be complex arc pathways (e.g., not a smooth path, but one varying in direction and curvature). An output arc field may fit within or near to the suggesting starting angles. Alternatively, the starting angles may be changed and unrelated fields may be produced.

While this sort of treatment planning process can provide optimized fields, it allows any suitable parameter to change, and may thereby provide a treatment plan that is unfamiliar to the user. For example, the starting angles may have been three angles from the left of the patient, but the optimized field may be an arc from the right side of the patient. The user may expect to see a few static fields, but may instead see arc fields (or vice versa). Also, the beam shape (e.g., MLC leaves) may be different than what is typically used. In other words, the algorithm may output fields that seem (to the user) completely different than the starting fields, or other treatments that have been used (and trusted) in the past.

If the user does not recognize the new treatment plan as at least similar to a previous trusted plan, the user may not understand why the new plan is better or how it is achieving the treatment goals, and the user may not willing to trust that the new plan is better. The user may be concerned that the algorithm did not operate properly, that the new fields may cause collisions with the treatment table, or that the new optimized plan may actually cause harm to the patient. As a result, the user may discard the new optimized treatment plan, and resort back to manual optimization techniques.

Further, this sort of treatment process may provide different optimized field for each patient. Two patients that both have similar diagnoses (e.g., a tumor to the right of the liver) may receive dissimilar treatment plans (e.g., due to different patient geometries or different optimization objectives). As a result, the user (e.g., dosimetrist or physician) may not grow accustomed to seeing a certain type of treatment plan, and thus may not be able to develop familiarity or trust in the optimization algorithm outputs.

Additionally, in order to fully optimize, the algorithm may try a number of different arc fields, static fields, and combinations. Thus, this process may also be a brute force type method that requires much time to complete.

Accordingly, there is a need for a treatment planning process that can produce optimized plans for specific patients while also being fast, flexible, and trustable to users.

III. Templates and Selective Tuning

Optimal treatment plans often include a combination of one or more arc fields and one or more static fields. In treatment plans that combine arc fields and statics fields, most of the dosage is typically provided by the arc fields. The static fields can then provide an additional dosage from additional angles in order to improve the quality of the total dosage.

For example, on the entire globe of possible radiation angles, there may be ranges of acceptable incoming radiation angles that are well-suited for arc fields (e.g., for a certain treatment). There may also be isolated small windows for incoming radiation (e.g., limited-range solid angles). These windows may accommodate a static field, but lack the range for an arc field. Additionally, it can be advantageous to use static fields for incoming radiation angles that are particularly safe or effective (e.g., good exposure of treatment area, and limited dosage to healthy tissue. A static field can maximize these particularly effective angles, as opposed to an arc field that may continually rotate, thereby spreading the dose over other angles that are less effective.

In this manner, arc fields and static fields can provide complementary doses with different characteristics. While static fields can take advantage of effective angles and limited windows, arc fields can provide a rounded dose. For example, with arc fields, radiation can be spread so that one portion of healthy tissue is not overexposed, and so that a tumor can be radiated from a variety of angles. In some embodiments, most of the dose is applied through the arc field, so that target area is mostly irradiated the same. Then, a minor portion of the dose can be applied through static fields, focusing extra dose through particularly good angles (e.g., for exposing the target area and avoiding OARs).

Optimal treatment plans can also include recycled arc field pathways. Arc field pathways that were optimized or effective for one patient can often be similarly optimized or effective for a second patient with a similar diagnosis (e.g., similarly shaped and located tumors). A trusted arc field pathway can often be slightly changed or exactly re-used for a new patient.

It can be advantageous to recycle known arc field pathways, as it can be risky to change an arc field pathway or create a new arc field pathway. An arc field covers a range of angles, so it can be difficult to immediately know if an arc field pathway has errors or disadvantages. For example, it is possible that a new arc field pathway can cause a radiation collision with a treatment bed, or deliver dosage incorrectly.

For at least the above reasons, in some embodiments, it is preferable to treat a patient with a combination of arc fields and static fields, where the arc field pathways are recycled known pathways, and the static field positions are specifically optimized for the patient. This can efficiently provide a high-quality treatment plan that is recognizable and easily trusted.

A. Templates with Initial Fields

Embodiments of the invention provide templates with initial fields for different types of treatments and target areas. For example, there may a template with initial radiation fields for patients with lung cancer, a template for patients with a brain tumor, and any other suitable type of treatment. Some embodiments provide additional templates based on tumor size and location and/or patient geometry.

In some embodiments of the invention, a template can include one or more initial arc fields (associated with one or more arc field pathways), one or more initial static fields (associated with one or more static field positions), and any other suitable field. For example, a template can include information for guiding an arc field, such as an arc field starting and ending position, as well as a pathway for the arc field to trace while radiation is being provided. Further, there can be any suitable number of static fields (e.g., 1, 2, 5, 10, or 15).

Templates can contain initial radiation fields that are proven, trusted, and/or clinically viable. In some embodiments, a user initially generates a template based on historical patient information (e.g., what fields were best in previous treatments). Templates can also be generated based on radiation spread (e.g., spatial gradients), other principles of physics, human anatomy, and any other suitable consideration. Typically, an experience physicist, treatment planner, or doctor will generate a template based on personal knowledge about the best field geometries.

A user may create a template by first adding an arc field (with a certain arc field pathway), and then adding static fields (with certain static field positions) that complement the arc field. Each field may cover different regions of possible incoming angles (e.g., each field may originate from a different portion of a sphere surrounding the patient). Accordingly, in some embodiments, the initial fields may not overlap with one another. As a result, each initial field (and later optimized field) may represent a unique and important dose contribution.

In some embodiments, a template can include constraints on the movement of the static field positions. For example, one or more initial static field positions may be adjusted to a better position for a specific patient. The static field positions may be constrained to move within a certain range of positions. In some embodiments, a static field position may be allowed to move within a certain constrained area on the surface of a sphere. The constrained area may be described by a solid angle of a certain size centered around the initial static field position. For example, the static field position may be allowed to move up to 3 degrees away the initial static field position (from the perspective of the isocenter).

Movement of the static field position may be constrained such that each static field position stays within an area that is considered a good region for hosting a static field. For example, it may be beneficial to have a radiation dose incoming from that general area (hence why that static field was included in the template in the first place). Further, keeping fields within a certain constrained region can prevent different fields from overlapping and interfering with one another.

Figure 3:
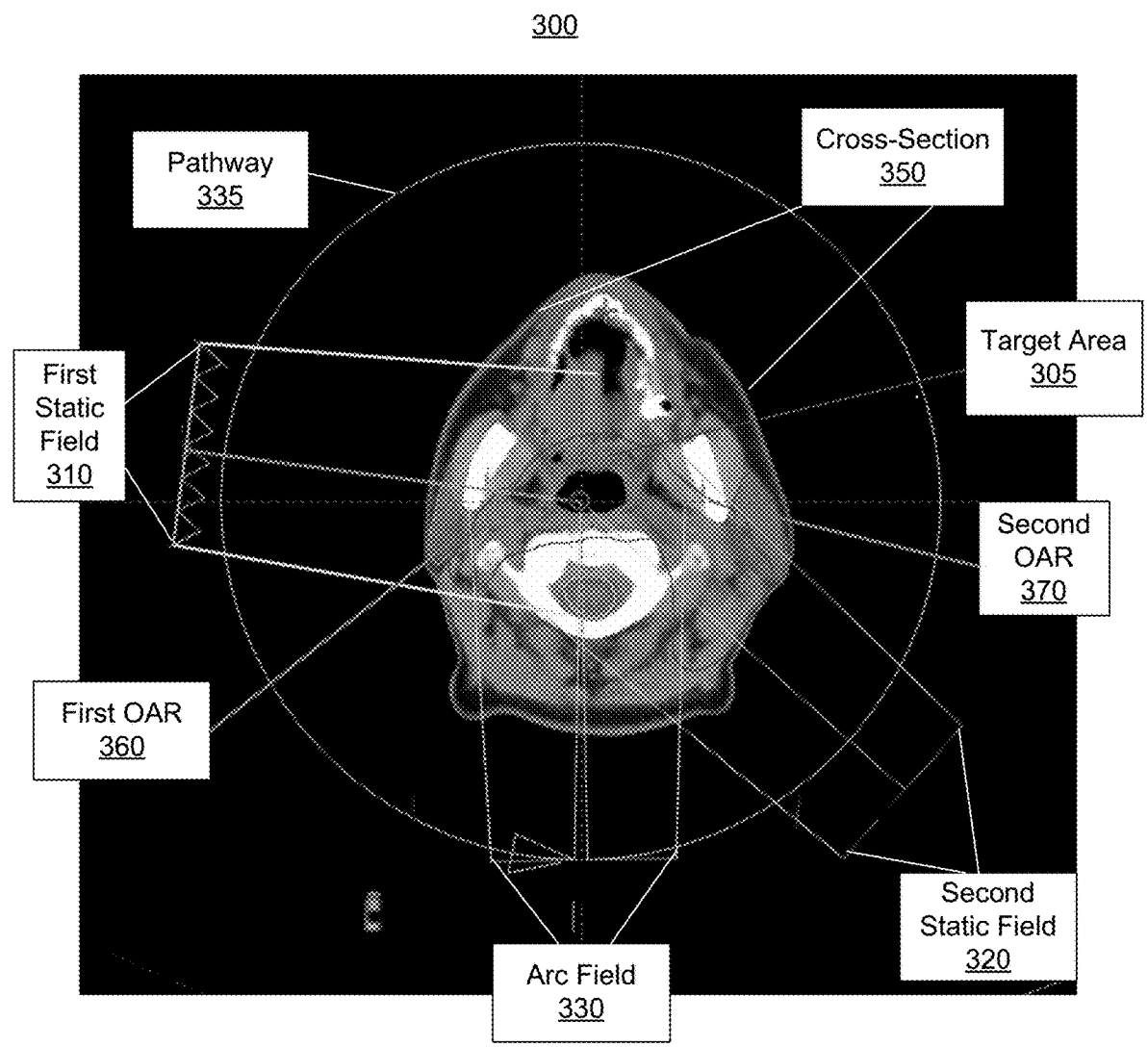
FIG. 3 shows an example of a treatment plan template, according to an embodiment of the invention.

An example of a template overlaid on a digital patient model is shown in FIG. 3. A template 300 with a first static field 310, a second static field 320, and an arc field 330 is shown. The first static field 310 may be permitted to move within the a first region (e.g., within three 10 degrees clockwise or counterclockwise) when used for a specific patient. Similarly, the second static field 320 may be permitted to move with a second region. The arc field 330 rotates around the patient along the pathway 335.

The template 300 is superimposed on a two-dimensional image of an example patient cross-section 350. The patient cross-section 350 can be a used as a reference when identifying a template for a new patient. For example, a new patient's tumor and body shape can be compared to one or more patient cross-sections 350 from one or more templates, and the template with the most similar patient cross-section 350 can be selected.

Each of the fields are directed toward a target area 305. A first OAR 360 and a second OAR 370 are also shown. The first static field 310 and the second static field 320 may be placed in positions that best irradiate the target area 305 while least irradiating the first OAR 360 and the second OAR 370.

In some embodiments, the initial arc field pathways in the template may not be allowed to change (or may have a limited range of adjustment). For example, as explained above, arc field pathways may be recycled for different patients without needing to be updated, and it may be undesirable to change arc field pathways due to risk. Initial static field positions, on the other hand, may be improved by fine tuning the position. For example, different patient geometries or slight differences in tumor size or shape may cause a scenario where a slight static field position change can improve the dose quality.

In some embodiments, a user may be able to change template parameters. For example, the user may be able to add, change, or remove static fields or arc fields for a certain patient.

In some embodiments, the template may also include approximate doses for each initial field in the template. Alternatively, the template may not include actual doses, but may instead suggest how to divide the total dose among the different fields (e.g., proportional doses).

B. Optimizing Static Field Positions

As mentioned above, when personalizing a template for a specific patient, it can be effective to optimize just the static field positions and keep the original arc field pathways (as initially set in the template). Each static field position may be restrained to a certain predefined region, and a static field position can be fine-tuned by moving it to an optimal position with the predefined region.

A static field position can be fine-tuned based on a number of factors. For example, the best static field position can be dependent on a patient geometry (e.g., body shape, internal tissue locations, etc.), estimated dose, estimated dose gradient, and any other suitable parameter. A description of how the static field positions are fine-tuned is given further below.

Figure 4:
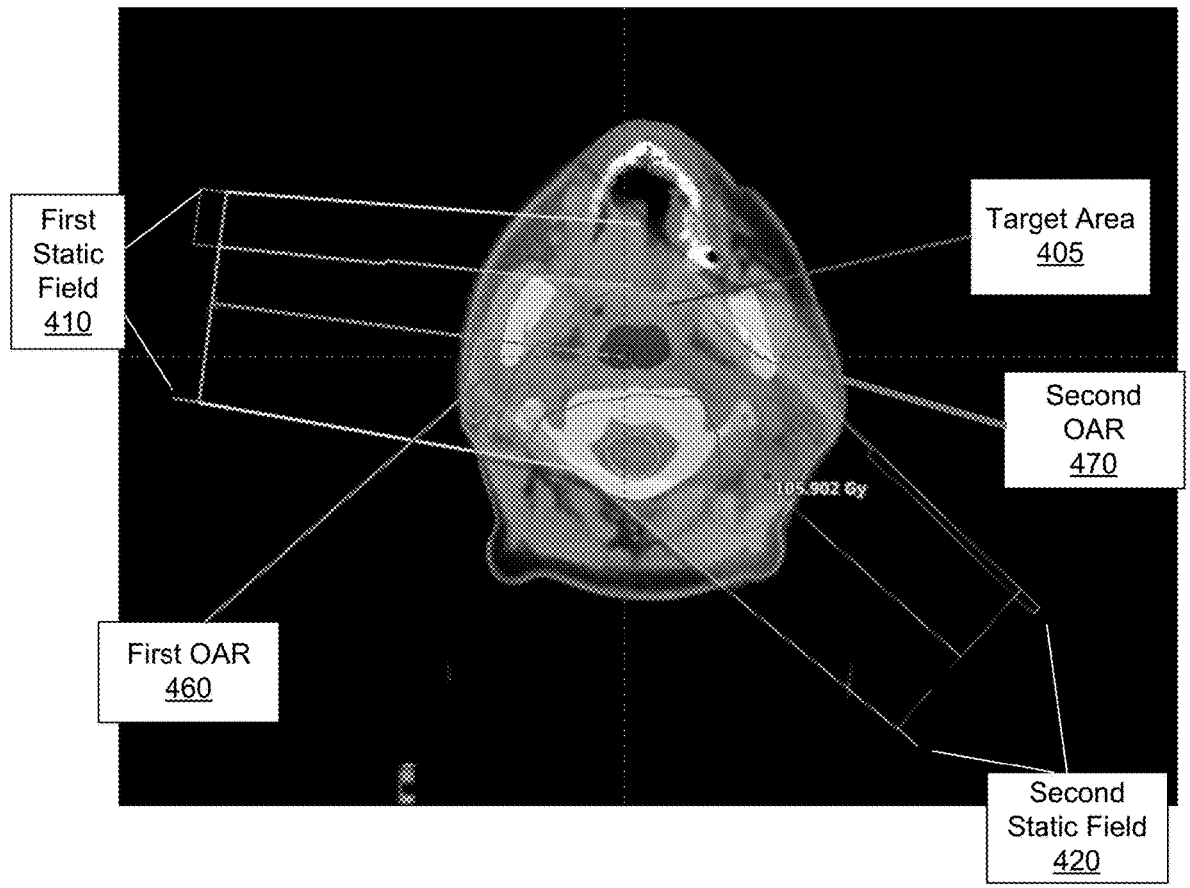
FIG. 4 shows an example of an initial treatment plan template that is not yet tuned, according to embodiments of the invention.
Figure 5:
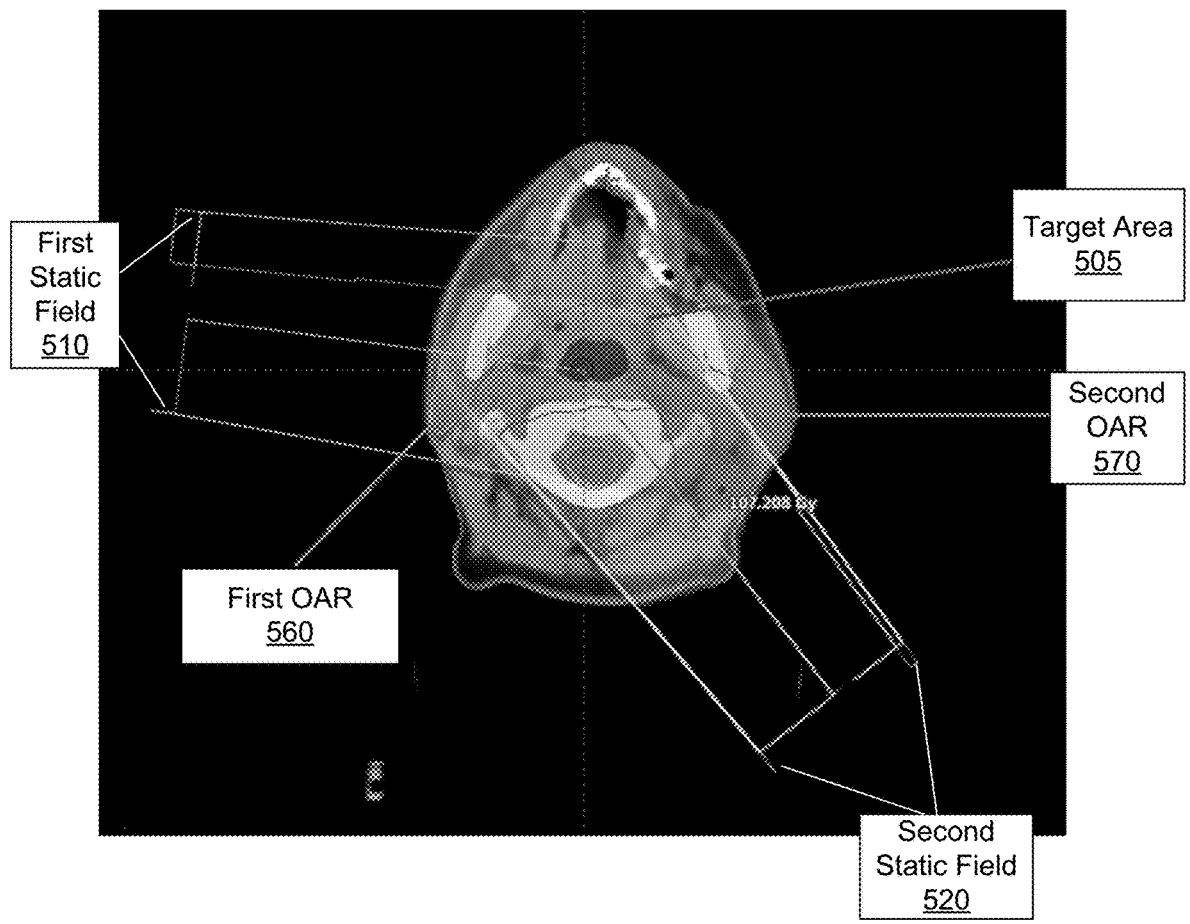
FIG. 5 shows an example of a treatment plan template that has been fine-tuned for a patient, according to embodiments of the invention.

FIGS. 4-5 shows an example of initial static field positions being fine-tuned for a specific patient. FIG. 4 shows a first static field 410 and a second static field 420, both in their initial template positions. The static fields are overlaid on an image of a patient cross-section. The template has just been applied to a patient model, so the static field positions are not yet tuned. While no arc field is shown here, one or more may be included in the template.

As shown in FIG. 4, the static fields irradiate the target area 405 with a total dose of 105.902 Gy. The first OAR 460 and the second OAR 470 lie within the beam paths, so they also receive some dosage. It is possible that these OARs have a different location or size than corresponding template OARs (e.g., the patient's body geometries may differ slightly from the average). Accordingly, the initial static field positions may cause more OAR irradiation than intended in the template. This could potentially be corrected by adjusting the static field positions.

FIG. 5 shows the same example as FIG. 4, but the static fields have been fine-tuned. The first static field 510 has not been moved, since the initial template position happened to be the optimal position for this patient. In other examples, the first static field 510 may be adjusted.

The second static field 520, on the other hand, has been rotated clockwise relative to the initial template position (e.g., the position of the second static field 420). As can be seen in FIG. 5, the radiation beam of the second static field 520 overlaps less with the OARs than the in FIG. 4. For example, the second static field 520 irradiates only the upper right portion of the first OAR 560 (as opposed to half of the first OAR 460 in FIG. 4), and the second OAR 570 is not irradiated at all (as opposed to the left side of the second OAR 470 in FIG. 4).

Additionally, the target area 505 now receives a greater dose of 107.208 Gy. Thus, the fine-tuned static field positions provide a dose that is more focused on the target area 505. More radiation is applied to the target area 505, while less radiation is applied to the OARs.

In some embodiments, most of the total dose can be provided by the arc field, and the remaining minor portion of the total dose can be provided by the static fields. Thus, adjusting the static fields can be a slight adjustment of how the dose is provided, such that the dose is tailored to a specific patient but not drastically changed. Accordingly, by starting with a trusted template and intentionally tuning the template field positions for a specific patient, field positions that are both optimized and trustworthy can be identified. Each static field may provide radiation to the treatment area from a different direction or in a different manner, and such that the dose is varied and static fields do not overlap.

In some embodiments, each field position can be fine-tuned and optimized independently. That is, the field positions may not interplay or affect one another. As described above, the field positions may each be assigned to a certain region of possible static field positions, and the regions may not overlap. Accordingly, each field position may be optimized based on what is best for a given independent region. This also means that it may only take one round of optimization to fine-tune each field position (e.g., the fields may not need to be iteratively adjusted based on one another).

In some embodiments, these adjusted field positions can be finalized and usable. They may be the best field positions for the given patient, and the field positions may improve the treatment plan quality (as compared to a plan using the initial template field positions). For example, even if a desired dose were to change, the field positions may still be optimally set.

C. Dose Gradient

In some embodiments, a static field can be fine-tuned based on a dose gradient. A dose gradient can describe how a dose distribution changes based on one or more radiation treatment system parameters. For example, a dose gradient can approximate the relationship between the field setup (e.g., the static field positions and arc field positions) and the relative dose received at each point in the patient.

Accordingly, dose gradient information can be used to determine what field positions can provide the most dosage to the treatment area, what field positions can provide the least dosage to various OARs and healthy tissue, what combination of field positions can provide uniform dosage to the entire treatment area, etc. This means that the dose gradient can be used to identify the best field positions for both exposing the treatment area and limiting dose to OARs.

A dose gradient can be derived from an approximated dose distribution with approximated dose values for each point in a patient's body. Accordingly, in order to determine a dose gradient, a mapping of approximate dose values to location may first be generated.

In some embodiments, a dose distribution can be generated for a certain template. The dose received at each point in a patient may be a summation of radiation from each radiation field. As a result, the field positions can determine the dose (or relative dose) received at each point. Accordingly, dose distributions may vary based on the template being used, and a dose distribution may be generated for a selected template.

The dose to be applied by each field in the template can be estimated. These doses can be divided portions of a total dose prescribed for a certain target area. These estimated doses may not need to be accurate, as they may just be used for measuring dose properties (e.g., relative dose given to different areas, dose fall-off, etc.). In some embodiments, a suggested doses associated with the template can be used.

The radiation dose received at a certain point can depend on a number of parameters. For example, the width and shape of the beam affects the volume of tissue that receives some dose. Also, as explained above, a spatial gradient may exist, such that a point on the edge of a radiation beam may receive a smaller dose than a point in the center of the beam. Further, the radiation intensity may decrease with depth in the patient's body, as the radiation may be partially absorbed by intervening tissue. Accordingly, a point deeper in the patient's body may receive a smaller dose than a point on the surface. The depth of a certain area (e.g., an OAR), and therefore the dose received at that area, can depend on the patient's geometry. Thus, the different doses received in different areas can be affected by the patient geometry and a number of field parameters, such as field position (e.g., distance and angle), beam shape, and radiation intensity.

A number of calculations and formulas can represent the above-described parameters. For example, the specific region irradiated in a patient can be described as a function of field position (e.g., gantry angle, treatment bed angle, and collimator angle) and beam shape (e.g., MLC leaf settings). Further, the relative dose received across a beam can be described by a spatial gradient formula. Also, there can be a function describing the dose received as a function of depth. As a specific example, dose as a function of depth can be given by:

$$D(z)=D_0 * e^{-rz}$$

where z is the depth, r is a radiation decay parameter, $D_0$ the dose at zero depth (e.g., the surface of the patient's body). This can also be described as a function of static field position parameters. For example, z can be measured as a distance within the body along a straight line coming from the radiation source position (e.g., z may not be the shortest distance to the patient body surface, instead it might be the distance to the body surface in a direction toward the beam collimator.)

A combination of the functions can be used to calculate the approximate dose for a specific point in the patient's body from a specific field. In other words, the total dose at a specific point from a given field can be a multivariable function that includes functional terms for field position, beam shape, and location depth (e.g., defined by patient geometry). The total dose received at a certain point can be estimated by adding the dose contribution from each field in the template. In some embodiments, each of these terms can be defined in terms of radiation field position parameters.

In addition to these formulas that approximate dose based on patient geometry and radiation field positions, some embodiments utilize a database of information about previous patients. For example, instead of calculating a dose, the dose distribution can be estimated using historical knowledge about doses used for previous patients with similar qualities (e.g., similar patient geometries and tumor geometries).

The dose received at a specific point can be represented by $$D_k = D_k(\{F_i\}_i)$$

where k represents a specific point, $D_k$ is the dose received at that point, $F_i$ refers to a set of all degrees of freedom associated with a radiation field i, and the curly brackets $\{\bullet\}_i$ refer to a set of all fields. In other words, the dose $D_k$ for a given point k can be considered a function of all the field parameters (that affect dose delivery) for each field in the template. All of the factors described-above that affect dose (e.g., depth, fluence, beam shape, etc.) can be counted for in this dose function.

The radiation field parameters can be divided into two set of parameters; "modulation parameters" and "field positioning parameters". The field positioning parameters can include parameters that affect field position, such as gantry position, treatment bed angle, and collimator angle. The modulation parameters can include other field-related parameters, such as MLC leaf settings and collimator settings that affect the beam shape and spread (e.g., fluence).

To demonstrate the different radiation field parameters, we can define:

$$F_i = \{\{p_{ij}\}_j, \varphi, \omega, \alpha, \vec{r}_0\}$$

where $\{p_{ij}\}_j$ a set of fluence pixel values (e.g., radiation flux) associated with the radiation field i, where $\{\bullet\}_j$ refers to a set of all fluence pixels associated to field i, where $\varphi$ is gantry angle, $\omega$ is collimator angle, $\alpha$ is the treatment bed angle, and $\vec{r}_0$ is the location of the radiation field isocenter. The modulation parameters can include $\{p_{ij}\}_j$, and the field positioning parameters can include $\varphi, \omega, \alpha,$ and $\vec{r}_0$.

With the above definitions, the total dosage at a certain point k as a function of field parameters can be more specifically described by:

$$D_k(\{F_i\}) = \sum_{ji} M_{kji}(\varphi, \omega, \alpha, \vec{r}_0) p_{ij}$$

where $M_{kji}$ is a coefficient describing the contribution from fluence pixel ij to dose at location $\vec{r}_0$. These coefficients are typically functions of the radiation field positioning parameters $\varphi, \omega, \alpha, \vec{r}_0$.

In some embodiments, it may be advantageous to simplify this dose estimation. For example, it may be beneficial to obtain a dose function that is only dependent on field position parameters. The modulation parameters can be reconsidered and optimized later on, after the field positions are set. As a result, the field positions may be separated and independent from changes in modulation parameters. This can significantly simplify the treatment generation process, as field positions can be maintained even if some other parameters are changed.

To simplify the dose function, values for the modulation parameters can be assumed. For example, we can assume static MLC leaf settings that produce conformal radiation beam, which then results in fixed fluence pixel values $\{p_{ij}\}_j$. This can remove the fluence pixel variable, and result in a dose function that is only dependent on field position parameters. For example, $D_k(\{F_i\})$ may be transformed into $\tilde{D}_k(\{\varphi, \omega, \alpha, \vec{r}_0\}_i)$.

In some embodiments, $\tilde{D}_k(\{\varphi, \omega, \alpha, \vec{r}_0\}_i)$ can be further determined based on historical patient data. For example, doses and modulation parameters that were used in previous treatments can be used to generate an estimated dose distribution.

$\tilde{D}_k(\{\varphi, \omega, \alpha, \vec{r}_0\}_i)$ represents a function of dose for a specific location based on field position parameters. More generally, the dose distribution can be expressed as $D = D(\vec{r}) \forall \vec{r} \in$ body. The approximate dose distribution is essentially a summation of the approximate dose for all points in the patient. The approximate dose for each point, and therefore the dose distribution, will change if the field position parameters change. In some embodiments, as $D = D(\vec{r}) \forall \vec{r} \in$ (and more specifically $\tilde{D}_k(\{\varphi, \omega, \alpha, \vec{r}_0\}_i)$) can be generated using any suitable dose prediction model.

$\tilde{D}_k(\{\varphi, \omega, \alpha, \vec{r}_0\}_i)$ can be used to estimate the dose received at the target area or a certain OAR. For example, by taking the summation of the estimated doses for each point within the parotid gland, the total dose received at the parotid gland can be estimated. The mean dose applied to the parotid gland can be expressed as:

$$D_{mean}^{parotid} = \frac{\sum_{k \in parotid} \tilde{D}_k v_k}{\sum_{k \in parotid} v_k}$$

where $D_k$ is the dose at a volume $v_k$ associated with a location $\vec{r}_k$, and summation is done over all locations $\vec{r}_k$ within the volume marked as part of the parotid gland. The above formula can be sufficiently accurate if the location sampling if dense enough (e.g., if the volumes $\{v_k\}$ are small enough to sufficiently approximate the volume of the parotid gland). The above formula is a simplified notation version of the following spatial integral:

$$D_{mean}^{parotid} = \frac{\int_{\vec{r} \in parotid} dr D(\vec{r})}{\int_{\vec{r} \in parotid} dr}$$

where dr is a differential volume element and integration is taken over the whole volume marked to belong to the parotid gland.

It may be an objective to minimize the dose provided to the parotid gland. To do this, the static field positions can be changed to new positions that result in less irradiation of the parotid gland. These field positions can be found by minimizing $D_{mean}^{parotid}$. In one embodiments, $D_{mean}^{parotid}$ can be evaluated multiple times with different radiation field position parameters. For example, different static field positions (within a region specified in the template) can be tested, and the lowest $D_{mean}^{parotid}$ can be identified.

Alternatively, the partial derivatives of $\tilde{D}_k$ can be used. The vector given by these partial derivatives is the dose gradient for the position k. For example, the dose gradient could be the following vector (in this example only one radiation field position is changed, and the isocenter location is left intact):

$$\nabla \tilde{D}_k = \begin{pmatrix} \partial_\varphi \tilde{D}_k \\ \partial_\omega \tilde{D}_k \\ \partial_\alpha \tilde{D}_k \end{pmatrix}$$

where $\partial_q \tilde{D}_k$ represents the partial derivate with respect to gantry position (and so forth). This dose gradient can provide a vector describing the direction of change (e.g., how to change one or more field position parameters) to so that dose is increased for that point (or the opposite vector can describe how to change parameters to decrease the dose at that point.

This dose gradient can be used to optimize (e.g., minimize) the mean dose at the parotid gland. For example, a gradient for the mean dose of the parotid gland can be determined by considering the effect of the dose gradient at each point within the parotid gland:

$$\nabla D_{mean}^{parotid} = \frac{\sum_{k \in parotid} \nabla \tilde{D}_k v_k}{\sum_{k \in parotid} v_k}.$$

An optimum (in this case minimum) value of the mean dose can be obtained by minimizing this gradient function. The dose gradient vector may be followed to a local minimum. For example, the an optimization function that minimizes an object function can be used, such as a deepest descent or simulated annealing function. While the optimization function may change the static field position parameters to minimize the mean dose, the optimization function may be constrained to optimize within the constrained static field position range (e.g., as specified by the template). Accordingly, the dose gradient can be incorporated into a cost function that, when minimized, provides optimized field position parameters.

This type of dose gradient-based optimization can also be performed for other OARs, as well as the target area. For example, in addition to minimizing the dose to the parotid gland, there may be another clinical goal of minimizing the dose to the mandible. Accordingly, a similar mean dose gradient function can be derived for minimizing the average dose to the mandible:

$$\nabla D_{mean}^{mandible} = \frac{\sum_{k \in mandible} \nabla \tilde{D}_k v_k}{\sum_{k \in mandible} v_k}$$

There may be any suitable number of optimization objectives, each of which can be modeled in this manner. For example, additional optimization objectives and mean dose gradient functions can be developed for the brain stem and for the target area. Each of these object-specific functions may take advantage of the same dose gradient matrix $\nabla \tilde{D}_k$. Typically, it is desirable to minimize the dose to OARs, and to maximize the dose to the target area.

$\nabla D_{mean}^{mandible}$, $\nabla D_{mean}^{parotid}$, mean and other similar mean dose gradient functions can be considered quality indexes. For example, the level of dose applied to the mandible or parotid gland can be associated with a quality score that is indicative of the treatment plan quality. It is likely that each of the quality index functions, if maximized or minimized independently, will produce different results. For example, the treatment plan that produces the best mandible quality (e.g., least dose to the mandible) is likely not the same as the treatment plan that produces the best parotid gland quality. In other words, different field positions may be best for different OARs and target areas.

Accordingly, the corresponding quality index functions may be evaluated together. For example, each quality index function may be assigned a weight, and the field position parameters (which affect each function) may be optimized based on the combination of the quality index functions and their assigned weights. A single cost function that considers each optimization objective can be expressed as:

$$C = \Sigma_i w_i ((Q_i - Q_i^{goal}))^2,$$

where $Q_i$ is a quality index (such as $D_{mean}^{parotid}$ $D_{mean}^{mandible}$), and where ($Q_i^{goal}$ is a goal value for a quality index. For example, a first goal may be achieving $D_{mean}^{parotid}$ of less than 2 Gy, a second mean goal may be achieving a $D_{mean}^{mandible}$ of less than 5 Gy, a third goal may be achieving a $D_{mean}^{target\ area}$ at least 50 Gy. The angular brackets indicate that the argument value is restricted to either larger or smaller than zero (depending on the quality of the goal). For example, for OARS, the goal is typically to reduce the related quality index below a maximum threshold value (e.g., minimize dose), while for a target area the goal is typically to exceed a minimum threshold value (e.g., maximize dose). If the threshold is not met, the quality score (e.g., output of the cost function) may be negatively affected. For example, if the mean dose of the parotid gland exceeds a maximum threshold value, the quality score may be penalized. The penalization may increase as the mean dose lowers (e.g., because it misses the threshold by a greater amount).

The relative importance of different goals are set by defining the weighting parameters $w_i$. Thus, if a certain change in a certain radiation field parameter simultaneously improves a first quality score of a first quality index (e.g., reduces $D_{mean}^{parotid}$) but negatively affects a second quality score of a second quality index (e.g., increases $D_{mean}^{mandible}$) the relative weights can determine which quality index takes priority, and therefore how to change the radiation field parameter. A weighting parameters may act as a multiplier for an organ-specific quality score or a target-specific quality score. Additionally, a weighting parameter may determine the magnitude with which a penalty (e.g., for not achieving a threshold) affects the quality score.

Thus, combining the quality indexes with their weights into a single cost function allows the net effect of parameter changes to be evaluated, and parameters can be optimized based on the best net position. The output of this cost function can be considered a net quality score that is based on the field position parameters, and minimizing the cost function can optimize the quality score (e.g., a lower output may be an optimal output).

Accordingly, a static field position can be fine-tuned based on information about patient geometry and dose gradient. Thus, the best field positions can be found without considering modulation parameters. As a result, the static field positions can be used for any set of modulation parameters, and may not need to be changed if new modulation parameters are being considered.

In some embodiments, each static field position can be optimized individually. For example, the dose distribution can be approximated with respect to the dose from one static field, and the above process can take place to optimize that dose distribution. In other embodiments, multiple static field positions can be optimized together. For example, the dose distribution can be approximated with respect to the dose from each static field. As a result, the approximate dose at each point can be a function of multiple position parameters for multiple static fields. Then, the above process can take place to optimize this dose distribution.

D. Tuning Static Fields Based on Dose Gradient

Figure 6:
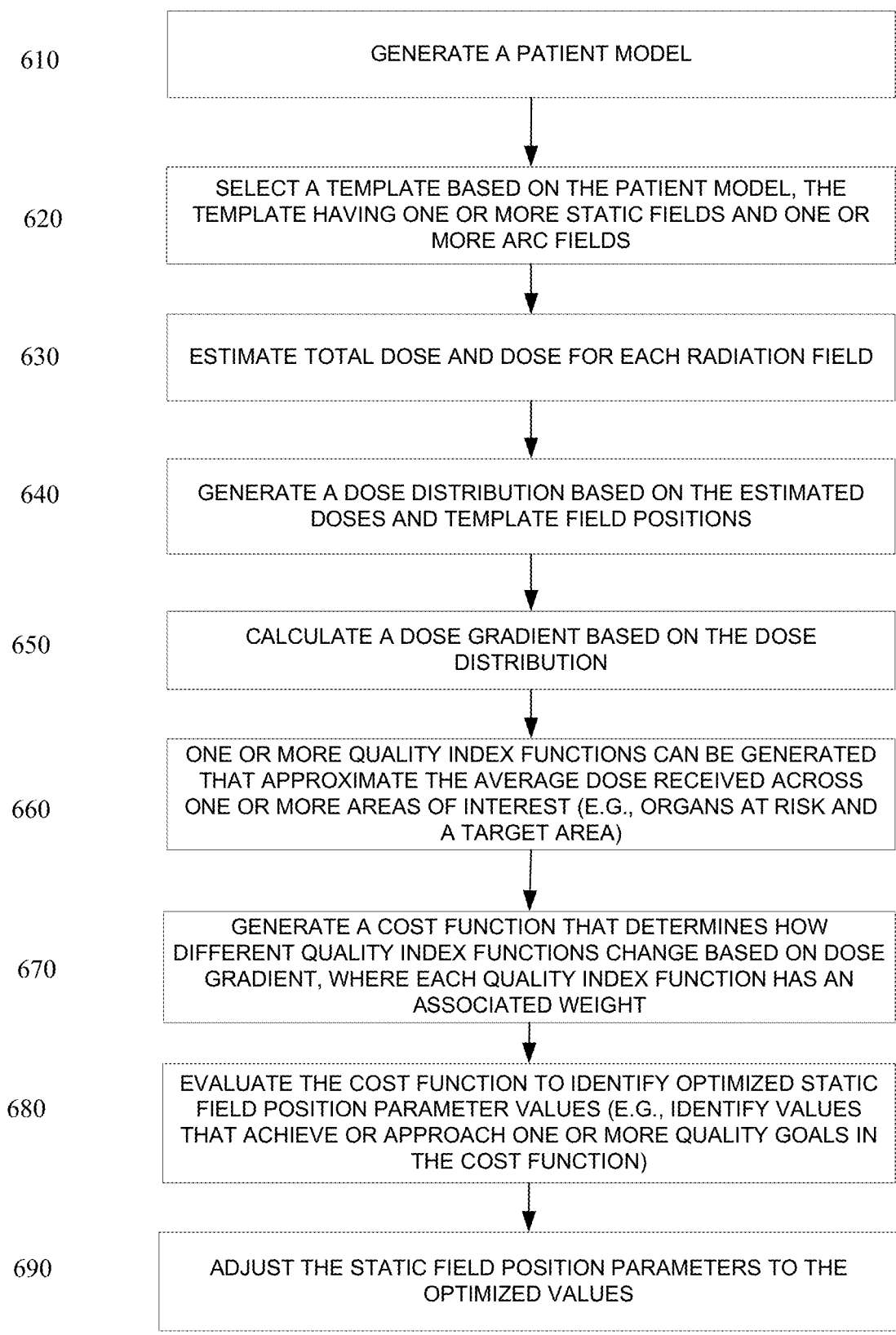
FIG. 6 shows a method for adjusting static field positions based on dose gradient.

FIG. 6 shows a method for fine-tuning static field positions based on one or more dose gradients.

At step 610, a model of a patient can be generated based on one or more patient images, measurements, and other structural information. For example, a series of CT scans with images of patient cross-sections can be layered and combined to form a three-dimensional patient model. The model can provide geometrical information of the patient, such as the sizes and locations of OARs and a target area (e.g., for irradiating a tumor).

At step 620, a template may be chosen based on the patient model and/or patient images. A template may be selected because it has a similarly located and/or shaped target area, and/or because the patient geometry is similar. The template may include one or more static fields (at one or more static field positions) and one or more arc fields (with one or more arc field pathways). The static fields may also have permitted regions (e.g., coordinate boundaries) within which they may be moved for a specific patient.

At step 630, the desired dose for the tumor may be estimated. The estimated dose may also be divided among different radiation fields in the template. The doses may be estimated based on a historical patient data, the size of the target area, and/or provided with the template.

At step 640, a dose distribution may be estimated. For example, a model may be developed based on the field positions, estimated field doses, and patient geometry that estimates how much dose will be applied to each point in the patient's body. The dose applied to each point can be affected by the depth of the point, how close the point is to the center of each field (e.g., radiation beam), and how far the point is from the radiation source (e.g., collimator), and how many fields irradiate the point. Each of these factors can be defined in terms of the field positions (e.g., the gantry position, treatment bed angle, collimator angle, etc.). Accordingly, the dose distribution can be defined in terms of the field positions.

At step 650, a dose gradient can be calculated based on the dose distribution. For example, partial derivatives can be taken for each field position parameter (e.g., gantry position, collimator angle, and treatment bed angle) to create a dose gradient matrix.

At step 660, one or more OARs and target areas with defined boundaries can be identified. Quality index functions can be generated that model the average dose to be applied to each of these regions. For example, the dose distribution can be summed over the volume of each OAR and target area.

At step 670, one or more cost functions can be generated. For example, the quality index functions can be defined in terms of the dose gradient. In some embodiments, a single cost function can be generated that uses dose gradient to evaluate multiple quality indexes. Weights can be assigned to each quality index, such that certain quality index goals can be prioritized while attempting to optimizing static field position parameters to values that satisfy multiple quality index goals.

At step 680, the cost function can be evaluated. For example, static field position parameters can be identified that achieve acceptably small OAR dose and sufficiently large target area doses. Thus, the static field position parameters may be changed in a direction that transforms the dose distribution as desired (e.g., increase dose to target area and decrease dose to OARs). The static field positions may be changed to optimize the dose distribution, but the arc fields may not be changed. The cost function may only change the positions within certain constrained regions as defined in the template (e.g., the static field position parameters may only be moved within allowed settings).

At step 690, static field position parameters may be changed to the optimized values. For example, the static field positions may be changed from the template positions, and the new parameters can be used to set new static field positions.

In some embodiments, one static field may be optimized at a time. For example, a dose distribution can be calculated based on a dose from one static field, and the dose gradient determined based on this dose distribution. Quality index functions describing the average doses to the target area and OARs can be generated based on the dose distribution, and the cost function can then be determined and optimized. This procedure can repeat for each static field.

This fine-tuning of the static field position can be accomplished by an automatic optimization system. For example, a template may be automatically chosen based on a patient model, the dose can be automatically estimated, the dose distribution and dose gradient can automatically be calculated, and the cost function can automatically be calculated and optimized.

After obtaining a field setup for a specific patient, the remaining treatment plan parameters can be optimized. For example, the radiation beam parameters (e.g., the MLC leaves and collimator settings) can be optimized based on the field positions and/or optimization objectives. The radiation beams can be formed so that the beam avoids OARs as much as possible while still irradiating the target area. Additionally, the total dosage can be calculated, and/or the distribution of the total dose among the different fields can be determined. The total dose can be determined based on the final field positions, optimization objectives, historical data for similar treatments, information about dose gradients or other physical principles, and/or any other suitable parameter. Any suitable method for determining dosages can be used (e.g., Monte Carlo methods).

E. Tuning Static Field Positions Manually

In other embodiments, the template static field positions can be adjusted manually. A user can look at geometry of the structures in a patient model or patient images. The user may be able to visually determine whether the template static fields will irradiate OARs. For example, a portion of the beam (e.g., an edge of a rectangular-based pyramid-shaped beam) may overlap with an OAR. The user may also see an alternative position that can be used for the static field, the alternative position having a more clear pathway to the target area (e.g., no OARs in the way). The user may change the static field to this alternative position.

This sort of field position adjustment can be entirely based on geometry. For example, the shape and geometry of the patient's body, target area, and fields can allow the user to rearrange the fields like a puzzle. The user may simply change the fields so that so that less OAR volume is exposed.

In some embodiments, this geometry-based optimization can be automated. For example, the volume of an OAR that is irradiated by a radiation field can be described by:

{volume(OAR) INTERSECT volume (collimated_beam)} where "INTERSECT" is a Boolean operator, where and "collimated_beam" is a radiation cone that has a peak at the radiation source and sides defined by the collimation jaws. This function can be summed over all the different radiation fields, and the function can be minimized. Minimization can produce beam cone locations that least-irradiate the OAR. The peak of the beam cone can be set as the field position (e.g., the gantry, treatment table, and collimator can be positioned to create this beam cone location).

F. Tuning Static Field Positions based on Knowledge Base

In addition to dose gradient, other factors can help with fine-tuning static field positions. For example, a knowledge base of information about previous patients and treatments can be used to fine-tune static field positions. A knowledge base may include information about patient geometries (e.g., body shape and size, organ locations and sizes, etc.), tumor attributes (e.g., size, location, shape), treatments applied (e.g., field positions used, dose applied, beam shape), treatment results (e.g., success rate, recovery time, side effects), and any other suitable information.

Knowledge base information can be used to identify the best treatments that have been used for a certain type of patient, as well as the likelihood of success and various side effects. It can also be determined whether certain radiation fields can cause unwanted results, such as exposure of a certain critical area of an OAR, or exposure a primary OAR instead of a secondary OAR.

In some embodiments, information about a current patient can be used to identify similar previous patients in a knowledge base. Previous patients may be identified with similar diagnoses (e.g., tumor shape, size and location), similar patient geometries (e.g., body shape and internal organ positions), similar demographics (e.g., patient age, medical history, gender, etc.), and with any other suitable similar qualities.

Then, information about treatments and results for the similar previous patients can be used for fine-tuning the static field positions for the current patient (as well as adjusting other treatment plan parameters). For example, the field positions used for previous patients can be used for the current patient. An average of the previous field positions can be used, or a set of field positions for a best-matching patient with the best treatment results can be used.

In some embodiments, a dose distribution can be generated for a patient as described above. Having the dose distribution, information in the knowledge base can be used to estimate how a dose-volume histogram may change for different static fields. For example, dose-volume histograms may be identified that were produced in treatments for previous patients with similar fields and patient geometries. Using this information, the static field positions with the best estimated OAR dose-volume histograms may be chosen.

In some embodiments, a mathematical model can be created based on information from the knowledge base. The mathematical model can describe relationships between input variables and output variables. For example, the mathematical model can provide an estimated treatment quality based on input patient geometry and tumor geometry. Further, the mathematical model can provide an estimated treatment quality based on different treatment plans and radiation fields. The mathematical model can indicate how a treatment quality may change as one or more static field positions are adjusted. The mathematical model may essentially provide a probability map of treatment quality for different field positions.

In some embodiments, a knowledge base and/or mathematical model can be used to fine-tune static field positions without determining or considering dose gradients. In other embodiments, the mathematical model can consider and incorporate dose gradient information (e.g., the model may be based on dose gradients for previous similar patients, or dose gradient for the current patient can be an input).

A knowledge base or mathematical model can also provide information about estimated doses. Doses used for previous patients can be used to determine what sort of dose can be achieved for the current patient. As a result, a mathematical model may allow a dose determination phase to be skipped, as recommended doses can be provided along with field positions by the mathematical model.

IV. Example Radiation Treatment System

Figure 7:
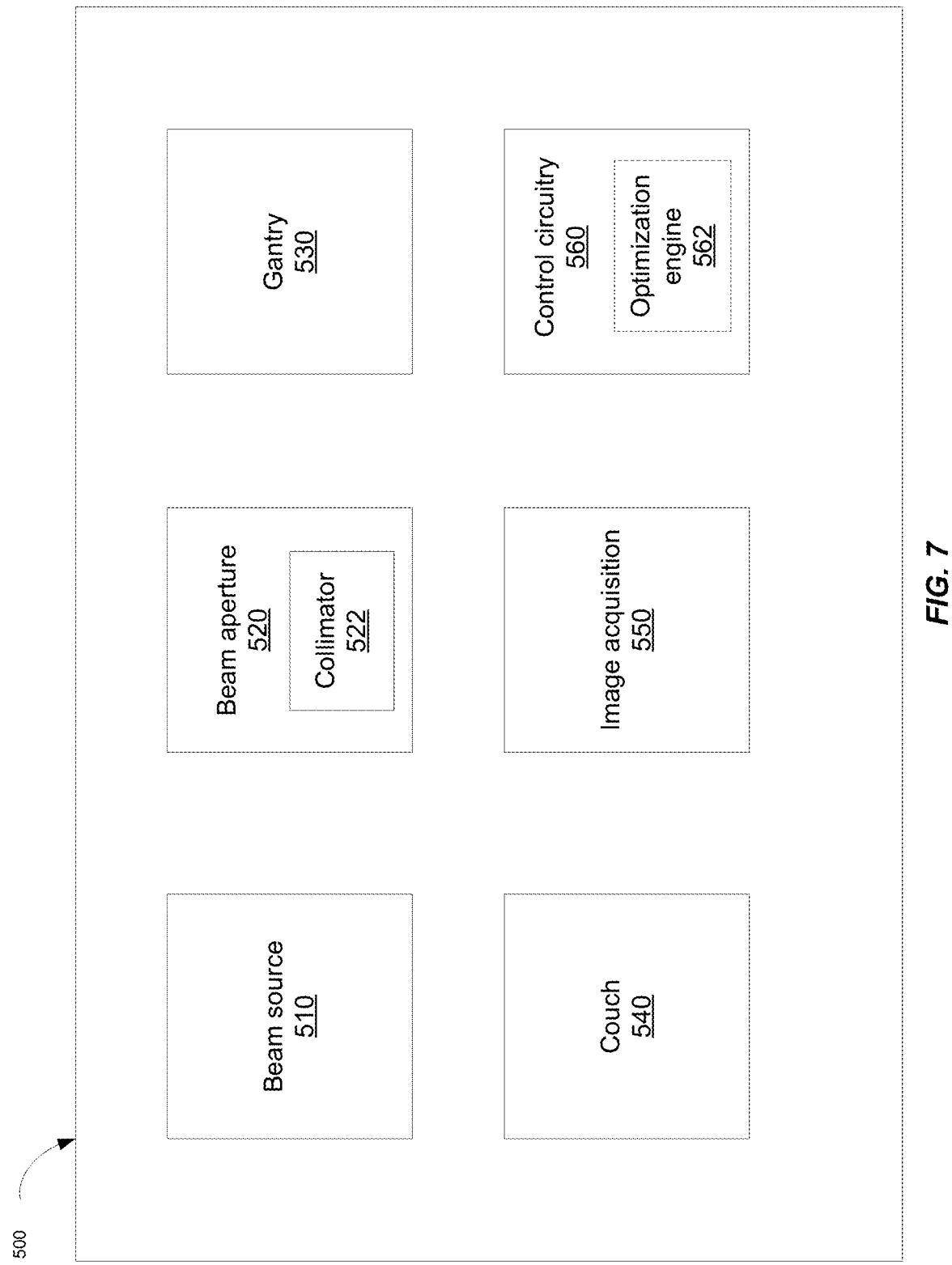
FIG. 7 shows a block diagram of a radiation treatment system of FIGS. 1 and 2.

FIG. 7 shows a block diagram of a radiation treatment system 500 for generating a treatment plan and implementing the treatment plan by providing radiation, according to embodiments of the invention. The system 500 can include components from the radiation treatment system shown in FIGS. 1 and 2. The radiation treatment system 500 includes a beam source 510, a beam aperture 520, a gantry 530, and a couch 540. The beam source 510 is configured to generate a beam of therapeutic radiation. This beam of radiation may include x-rays, particles, and the like. The beam aperture 520 includes an adjustable multi-leave collimator (MLC) 522 for spatially filtering the radiation beam. The couch 540 is configured to support and position a patient. The couch 540 may have six degrees of freedom, namely the translational offsets X, Y, and Z, and the rotation, pitch, and yaw.

The gantry 530 that circles about the couch 540 houses the beam source 510 and the beam aperture 520. The beam source 510 is optionally configured to generate imaging radiation as well as therapeutic radiation. The radiation treatment system 500 may further include an image acquisition system 550 that comprises one or more imaging detectors mounted to the gantry 530.

The radiation treatment system 500 further includes a control circuitry 560 for controlling the operation of the beam source 510, the beam aperture 520, the gantry 530, the couch 540, and the image acquisition system 550. The control circuitry 560 may include hardware, software, and memory for controlling the operation of these various components of the radiation treatment system 500. The control circuitry 560 can comprise a fixed-purpose hard-wired platform or can comprise a partially or wholly-programmable platform. The control circuitry 560 is configured to carry out one or more steps, actions, and other functions described herein. In some embodiments, the control circuitry 560 may include a memory for receiving and storing a radiation treatment plan that defines the control points of one or more treatment fields. The control circuitry 560 may then send control signals to the various components of the radiation treatment system 500, such as the beam source 510, the beam aperture 520, the gantry 530, and the couch 540, to execute the radiation treatment plan. In some embodiments, the control circuitry 560 may include an optimization engine 562 configured for determining a radiation treatment plan. In some other embodiments, the control circuitry 560 may not include an optimization engine. In those cases, a radiation treatment plan may be determined by an optimization engine in a separate computer system, and the radiation treatment plan is then transmitted to the control circuitry 560 of the radiation treatment system 500 for execution.

In some embodiments, the optimization engine 562 may be configured to determine a radiation treatment plan including specific instructions for the components in the radiation treatment system 500. For example, a radiation treatment plan may include instructions for moving the gantry 530 to a certain position for a certain amount of time, instructions for implementing beam aperture 520 settings, instructions for moving the couch 540 to a certain position for a certain amount of time, instructions for controlling the beam source 510 to emit a radiation for a certain amount of time, and/or any other suitable instructions.

V. Example of Generating and Applying a Treatment Plan

Figure 8:
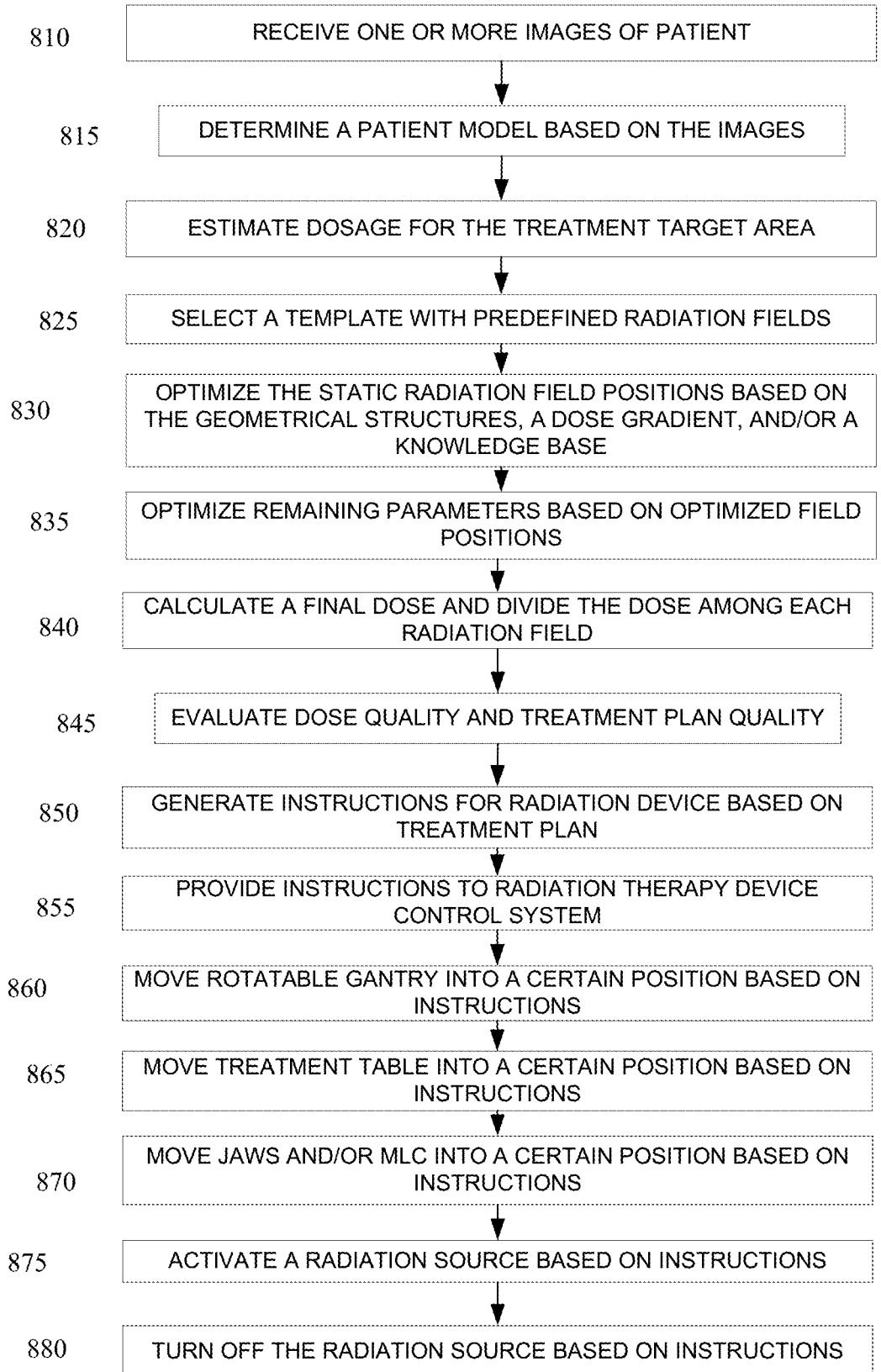
FIG. 8 shows a method for generating and applying a treatment plan, according to embodiments of the invention.

An example of generating a treatment plan and implementing the treatment plan by providing radiation, according to embodiments of the invention, is shown in FIG. 8.

At step 810, a user (e.g., a dosimetrist, physician, or technician) may capture and/or receive images of a patient, and/or otherwise receive information about a patient. For example, one or more CT scans of the user may be obtained. The CT scans may include information about a patient tumor and locations of healthy patient tissue and organs.

At step 815, the user may determine a patient model (e.g., a three-dimensional model) based on the images and/or other patient information. Structures (e.g., tissue structures and tumors) within the patient may be shown in patient images (e.g., CT scans). The user (or an automated computer) may define three-dimensional structure models based on the images. For example, multiple images covering different two-dimensional cross-sections can be combined to create a three-dimensional model. The structure set can include a three-dimensional mapping of the patient's organs (including OARs), the patient's body outline, and any other suitable information. The patient model may also include information about a size, location, and shape of a tumor (or other radiation targets) within the patient body. Other information, such as anatomy knowledge or additional overlaid images (e.g., MM images) can also be used for the model.

At step 820, a radiation dosage for the treatment's target area (e.g., a tumor identified in the patient model) can be estimated. The dosage may be based on the size and shape of the target structure. The dose may be refined later, and an approximate dose can be used at this point. The user may also estimate the fractionation and energy level to be implemented.

Additionally, an isocenter may be determined for the patient's treatment area. The isocenter may be the geometrical center of the tumor, the tumor's center of mass, or any other suitable point that can serve as a central treatment point (e.g., a point around which the gantry can rotate during treatment).

The user may also develop one or more optimization objectives for the treatment. For example, the user may generate a proposed dose volume histogram (DVH) for one or more organs, estimating an acceptable (e.g., maximum allowable) radiation amount for the organs. Some OARs may be considered particularly sensitive or at risk, and may only safely receive a small amount of radiation. With information about the desired tumor dose and acceptable healthy tissue dose, the user (or system) can develop a desired dose distribution for the patient. In some embodiments, the dose distribution can include a spatial mapping of maximum and/or minimum dosage to different regions of the patient's body. A dose distribution can also be obtained through a dose prediction model.

At step 825, the user may select a template with one or more radiation fields (e.g., arc fields associated with certain pathways, and/or static fields associated certain positions). A template can be selected based on the patient's type of ailment, tumor details (e.g., size, shape, location), the patient's body shape, or any other suitable factors. For example, a template for prostate cancer may be selected for a patient with prostate cancer. The selected template may be centered on the isocenter. For example, the template can be virtually overlaid onto the patient model or patient images.

At step 830, the template may be optimized for the current patient. Static field positions can be optimized through one or more techniques. For example, a user can manually change static field positions based on geometrical information about the patient structures and fields. The user may move static fields to positions that irradiate OARs less and the target area more (this may not require any information about doses or optimization objectives).

Static field positions can also be fine-tuned using dose gradients. For example, doses for each field can be approximated, a dose distribution can be approximated based on initial static field positions and doses, and then a dose gradient can be derived from the dose distribution. Quality index functions can be generated that express how the average dose on volumes of interest (e.g., OARs and target area) are affected by changing the dose distribution (as described by the dose gradient). A cost function can be assembled that considers each of the quality indexes, assigns a weight to each, and compares each quality index with an associated goal. Then, the cost function can be evaluated, thereby identifying optimized static field position parameters that meet each goal (or at least move toward each goal, based on the weights). For example, optimization can change the dose distribution so that OARs receive less dosage and the target area receives more dosage.

Static field positions can additionally be fine-tuned based on information from a knowledge base. For example, dose distributions for different static field positions (within an allowed range) can be estimated based on historical treatment data (e.g., from patients with similar target areas and/or OAR shapes and locations). The static field positions with the best estimated dose distributions can be selected.

In some embodiments, one or more arc field pathways may also be adjusted for the patient. For example, the rotation of the arc pathway may be reversed (e.g., while the arc pathway location may stay the same). The user may review the fine-tuned field positions (e.g., for static fields and arc fields) to check whether they are acceptable. As a result, the radiation field positions can be personalized for the current patient.

At step 835, the remaining treatment plan parameters can be optimized. For example, the modulation parameters, such as MLC leaf settings that define the shape, spread, and characteristics of the radiation beam, can be optimized for the patient. Radiation fields can be manipulated so that they expose more of the target area and less of the OARs (e.g., without changing the field positions).

At step 840, the final dose values can be calculated. The total target dose and the division of the dose among different radiation fields can be determined or adjusted based on the final field positions. In some embodiments, a second optimization algorithm can divide the total dose among the fields. Alternatively, the user can manually test different dose divisions to determine what field setup is preferred.

At step 845, the user can review the radiation fields and doses to evaluate whether the treatment plan is acceptable. For example, the user may determine and evaluate a treatment plan quality. If desired, the user can adjust the doses or fields. The user may decide to choose a different template and try the optimization process again. This time the user may have the static field positions fine-tuned based on different information, or the user may input different optimization objectives. Also, the user may add or subtract a field from a template, or change the constrained area within which a static field in a template can be positioned.

Once the user approves a final treatment plan for the patient, the treatment plan can be implemented. The remaining steps in the method describe generating machine instructions and providing radiation.

At step 850, instructions for controlling a radiation treatment system can be generated based on the treatment plan. For example, instructions for controlling a gantry, treatment head, collimator, power source, MLC, or any other instruments can be generated that implement the approved treatment plan. The instructions can be used to control the radiation treatment system so that radiation is applied to the patient from the indicated arc fields (at indicated arc field pathways) and static fields (at indicated static field positions) with the determined dosages.

At step 855, the instructions can be transmitted to a control system (e.g., control circuitry) of a radiation treatment system. As mentioned above, the treatment planning process and optimization can take place at a computer or software module that is a part of a radiation treatment system. Alternatively, the treatment planning can happen elsewhere (e.g., at a separate computer), and then instructions designed specifically for the radiation treatment system can be transmitted to the radiation treatment system.

In the following steps, the radiation treatment system can implement the treatment plan by providing radiation to the patient. The various instruments in the radiation treatment system can be coordinated to deliver radiation from one or more indicated arc field pathways and static field positions.

At step 860, the control system can move the rotatable gantry to a position indicated in the treatment plan instructions. For example, the rotatable gantry can be set to a position associated with a static field or a beginning position of an arc field.

At step 865, the control system can tilt the treatment table to a position indicated in the treatment plan instructions. For example, the incoming radiation angle can be created by combining a certain treatment table position and rotatable gantry position. A collimator angle can also be adjusted.

At step 870, the control system can adjust the jaws and/or MLC based on the treatment plan instructions. Accordingly, the radiation beam can be shaped appropriately when emitted.

At step 875, the control system can activate a radiation source (e.g., a high voltage source for an electron gun) based on the treatment plan instructions. As a result, radiation can be applied according to a power level and time duration indicated in the treatment plan.

Further instructions can control the radiation treatment system to move the radiation beam and apply radiation from other fields with other positions. For example, at step 875, if radiation is being applied from an arc field, the control system can move the rotatable gantry along an arc field pathway. The control system can keep the radiation source active during the arc.

At step 880, the control system can stop the radiation source, and reposition the radiation treatment system for another field. For example, the rotatable gantry and treatment table may be adjusted for providing radiation from a second field (e.g., a static field) with a second position. These steps can continue until the treatment plan is completed.

In some embodiments, one or more of the above-described steps can be automated, instead of being performed by a user. For example, a user can select a treatment template, and then the steps of fine-tuning field positions and optimizing doses for the fields can happen automatically. Even further, the earlier steps of selecting a template, estimating dose, developing optimization objectives, and/or generating a patient model can be automated. For example, patient images can be analyzed to develop a patient model, a tumor can be identified in the model, and the template can be selected based on the tumor location.

Embodiments of the invention provide a number of advantages. For example, using a template with trusted (e.g., clinically proven) initial field positions instills trust and understanding into the user. Embodiments still allow changes in the template so that the treatment plan can be optimized for a specific patient. However, constraining the field positions maintains the user's trust in the treatment plan, since a fine-tuned static field position may still appear similar to the initial template.

Additionally, while a template's field positions can be optimized, each individual arc field and static field can be maintained (e.g., instead of removed or adjusted to a different region). Accordingly, proven field regions are still utilized. Also, since arc fields and static fields may not be interchanged, an optimized treatment plan can always include a combination of field types (which can be preferable).

Embodiments allow each field position to be fine-tuned independently. This can create an efficient optimization process, as different field positions may not need to be considered in combination (thus making optimization more simple) This also allows each field position to be set after just one round of optimization (e.g., multiple iterations may not be needed). Instead of guessing what new field positions might be better (as done in previous techniques), each field position can be quickly optimized within its allowed position range.

Further, some embodiments allow radiation field positions to be fine-tuned to a preferred position independent of an intended dosage (in contrast with previous techniques, where dosage and field positions are typically interdependent). This streamlines the treatment plan generation process, as field positions can be kept the same even if the doses or optimization objectives are changed (in contrast with previous techniques, where changing the dose or optimization objectives might require re-optimizing the field positions). Thus, a treatment plan can be generated more quickly and optimized more fully.

VI. Transforming Treatment Plans

Embodiments of the invention provide special treatment techniques for more complicated scenarios. For example, methods are provided for leveraging an existing plan for a similar diagnoses in a different area. Additionally, methods are provided for dividing or combining treatment plans based on unusually sized or shaped treatment areas.

A. Leveraging Existing Template for New Location

Some tumors and treatment areas can be similar to one another. For example, since the human body is approximately symmetrical (left side and right side), an arm or other tissue mass on one side may be similar to (e.g., mirrored by) another arm or tissue mass on the other side.

Accordingly, it may be possible to leverage a template or treatment plan from one side of the body for use on the other side. For example, a user may seek a template for a tumor in a patient's right hip. However, a template may only be available for the left hip. In some embodiments, the user may be able to use the left hip template for generating a treatment plan for the right hip.

Copying over a template in this manner may be done if the tumor or isocenter in the right hip is sufficiently similar to the tumor or isocenter associated with the template for the left hip. A human operator may decide if the tumors or locations are similar enough to utilize the template. For example, the operator may ensure that all the template fields, when copied over to the right hip, have a clear view of the target area (e.g., they are not blocked by the treatment bed, the patient's arm, or any other barrier). The operator may also check that the fields can expose the entire target area (e.g., the target area is not too large to be fully covered by the fields).

In another example, a patient may have two tumors in symmetrical locations. One tumor may be in the patient's left breast, and the other tumor may be in the patient's right breast. The user may first develop a treatment plan for the left breast. Then, instead of going through another entire treatment planning process for the right breast, the left breast treatment plan may be copied over for use in the right breast (e.g., if the tumor and/or isocenter are sufficiently similar).

Adjustments or transformation can be applied to a treatment plan or template that is copied to another area, as described above. For example, the template for the left hip may be transposed for use at the right hip (instead of just copied). This can include linearly transforming (e.g., rotating and/or mirroring) radiation fields from the left hip template. A static field for the left hip may have provided radiation from the left side of the patient. When the template is converted to match the right hip, the static field may now be provided from to the right hip from the right side of the patient (e.g., in an equal and opposite manner).

More generally, after adding a new isocenter at the right hip, a mathematical operation can be applied to the entire left hip template to obtain the right hip template for the right hip isocenter. The mathematical operations can include a rotation matrix (e.g., rotating the radiation field position parameters), a translation matrix (e.g., moving the radiation field position parameters), and a scaling operation (e.g., adjusting the collimator opening to expand or contract the beam size). These transformations can be based on the relative position, orientation, and size of the new tumor and isocenter to the original tumor and isocenter (for which the template is designed). For example, a transformation can be determined that would transpose a first isocenter to a second isocenter. Then, the determined transformation can be used to transform the template (e.g., the field position parameters). The transformations are applied to the "seed" (i.e., original) isocenter, all the control points that establish the coordinate space around that isocenter, and field positions (e.g., beam vectors) within the coordinate space.

Figure 9:
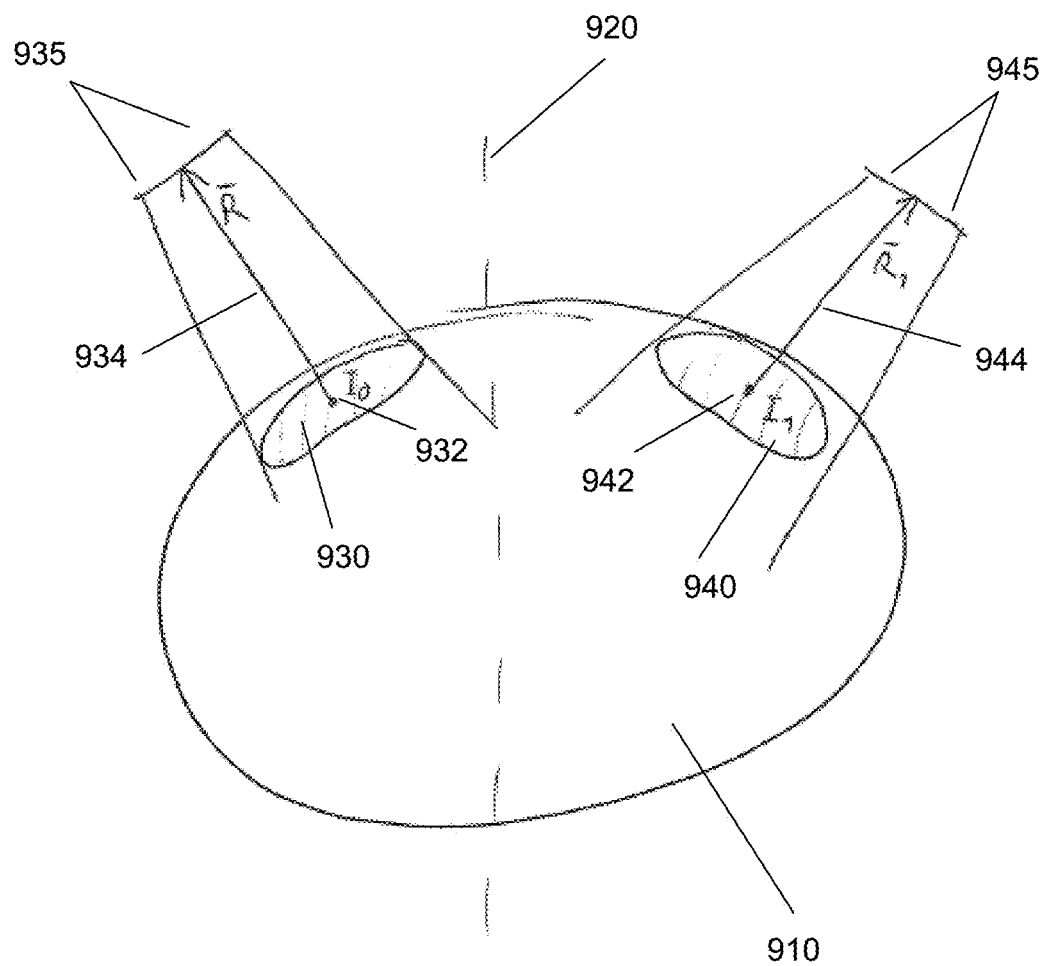
FIG. 9 shows an example of translating a template for one region for use in another region, according to embodiments of the invention.

FIG. 9 shows an example of a template (or treatment plan) being transposed onto a new location. A liver 910 may have a first tumor 930 and a second tumor 940. A template with a first static radiation field 935 incoming from a first direction 934 may have been designed for the first tumor 930. The template may be centered at a first isocenter 932. The first direction 934 of the first static radiation field 935 may be set as the normal direction from the surface of the first tumor 930 or the direction that is normal to the surface of the liver 910 at that point.

The user may copy the template over to the second tumor 940. In some embodiments, the template may be reflected across a liver bisecting line 920. For example, the first isocenter 932 may be copied to the opposite side of the bisecting line 920 at the same distance to create the second isocenter 942 (e.g., if the bisecting line 920 is the x-axis, the x-coordinate of the first isocenter 934 can be reversed). Similarly, the a second static radiation field 945 may be oriented in a second direction 944 that is a reflection (across of the bisecting line 920) of the first direction 934. This way, the initial relation between the first static radiation field 935 and the first target area can be reproduced for the second static radiation field 945 and second target area. In alternative embodiments, the second direction 944 can be set as the direction that is normal to the surface of the liver 910 as the second isocenter 942 (e.g., if the first direction 932 was also normal to the surface of the liver 910).

When a template or treatment is transformed for use in another area, optimization may take place for the new location. For example, the initial template static field positions for the new right hip template (e.g., obtained through transformation of a left hip template) may be fine-tuned, as described above. For example, the step of copying over and applying a template can take place between steps 825 and 830 in FIG. 8. Thus, if there are differences between the geometry of the left hip and right hip, these differences can be accounted for by fine-tuning the field positions and doses.

In some embodiments, existing templates and treatments can be copied to any comparable area (e.g., not just a symmetrical location). For example, a template for treating skin cancer in the upper arm may also be usable for treating skin cancer in the forearm. Mathematical operations based on the difference between a first location (e.g., upper arm) and a second location (e.g., lower arm) may be applied to a template that is being copied from the first location and the second location.

B. Divide One Isocenter into Multiple Isocenters

Some treatment areas can be especially large due to a large tumor or a tumor that is spread throughout different areas. For large treatment areas, one isocenter may be insufficient for providing radiation to the entire treatment area. For example, a treatment area may be long and narrow (like a tall cylinder). Radiation aimed at one isocenter on the cylinder may only be able to provide radiation to a portion of the treatment area. Accordingly, in some embodiments, multiple isocenters can be placed for one treatment area.

Figure 10:
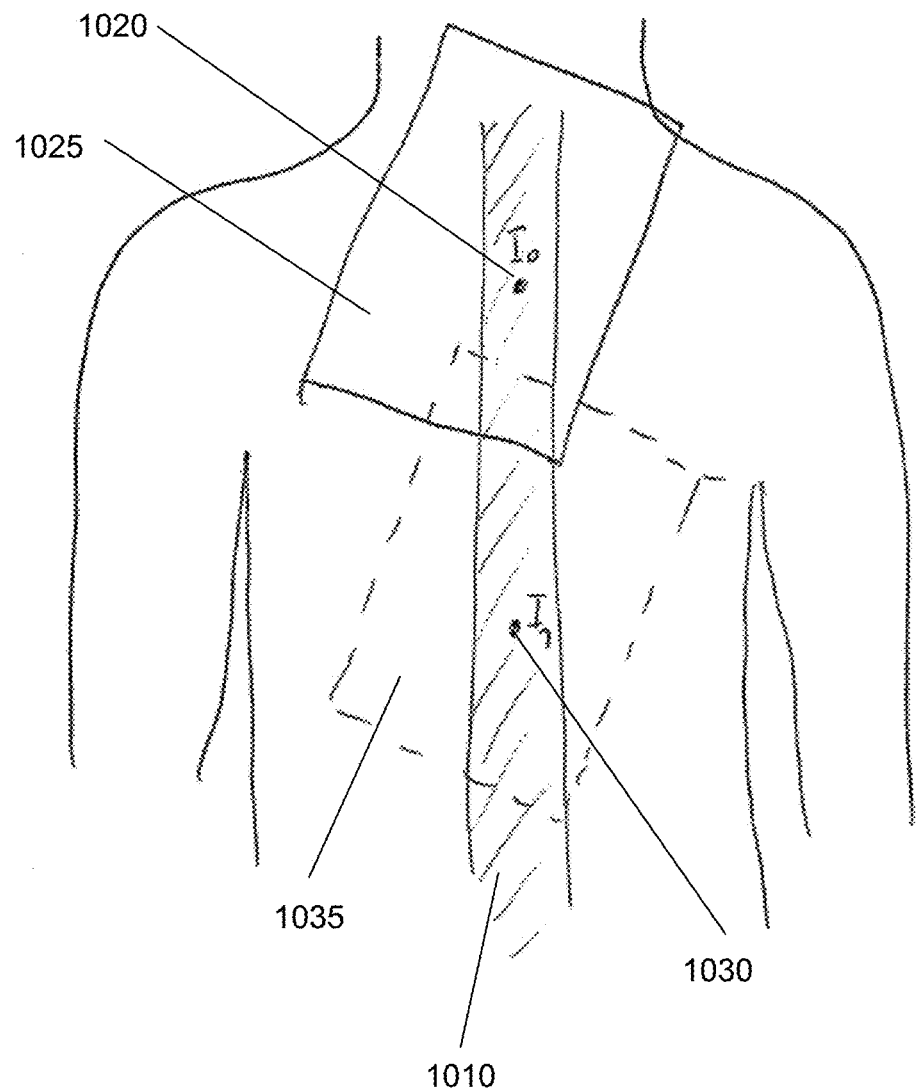
FIG. 10 shows an example of using multiple isocenters for one target area, according to embodiments of the invention.

An example of a single treatment area with multiple isocenters is shown in FIG. 10. A patient's spine 1010 may call for multiple isocenters along the patient's longitudinal axis to create full coverage. A first isocenter 1020 can be placed in the top half of the spine. Radiation fields for the first isocenter 1020 may be able to irradiate within a first area 1025. A second isocenter 1030 can be placed in the bottom half of the spine. Radiation fields for the second isocenter 1030 may be able to irradiate within a first area 1035.

A template with one or more radiation fields may be created for the first isocenter 1020. For example, there may be an arc field that circles the first isocenter 1020. The first isocenter 1020 and corresponding template may then be copied and translated 20 cm down along the longitudinal access, thereby establishing the second isocenter 1030. As a result, the template radiation fields (e.g., the arc field) may be reproduced 20 cm below the first set of template radiation fields to create a new set of radiation fields.

Fields and doses for each isocenter can then be optimized, as explained above. In some embodiments, some field parameters and/or doses may differ between the two treatment plans, as the different portions of the target area may have some difference.

C. Combine Multiple Isocenters into One

In some embodiments, multiple treatment plans for different treatment areas (e.g., different tumors) can be combined into one treatment plan for all the constituent treatment areas. This can include folding multiple isocenters into one isocenter, which may be located in between the constituent isocenters.

In one example, two treatment plans for two different tumors may both involve a similar field geometry. For example, the same static field may be used for both tumors. This means that, from the perspective of that static field, one of the tumors is directly in front of the other. As a result, radiation intended for the first tumor will also provide a dose to the second tumor (if sent from the common static field). In this case, the static field can be removed from one of the tumor's treatment plans, as the static field can be used once to expose both tumors. In some embodiments, this can happen by combining both of the treatment plans into one treatment plan.

In some embodiments, there may not be perfect overlap between two fields, or the beam shapes (e.g., a diverging radiation cone) may not perfectly intersect. However, if there is sufficient overlap (e.g., 90% beam cross-sectional or beam volume overlap), the radiation fields may be combined. A user may typically decide whether there is sufficient overlap for combining two fields into one. A combined field may be fine-tuned and the beam size (e.g., via MLC settings) adjusted so that both tumors are exposed, and so that OAR exposure is minimized.

Additionally, an arc field from the first tumor may lie in the same plane as another arc field from the second tumor. Accordingly, these two arc fields can be combined into one arc field. For example, a first 180 degree arc angle for a first tumor may be equal and opposite to a second 180 arc angle for a second tumor. These can be combined into a full 360 degree arc angle (and the beam collimation shape can vary according to the constituent angles). However, if the constituent arc fields do not cover the entire 360 degree range, the radiation beam may turn off in a middle portion of the newly combined arc field in an area where neither constituent arc field existed.

Two radiation fields that are adjacent, but not completely overlapping, can also be combined. For example, there may be two isocenters that are adjacent, and both may be radiated from directly above by rectangular beams. As a result, the two rectangular beams border one another or have some overlap. These two beams can be combined into one larger rectangular beam (e.g., if MLC movements enable a larger beam shape).

D. Example of Transforming a Treatment Plan

Figure 11:
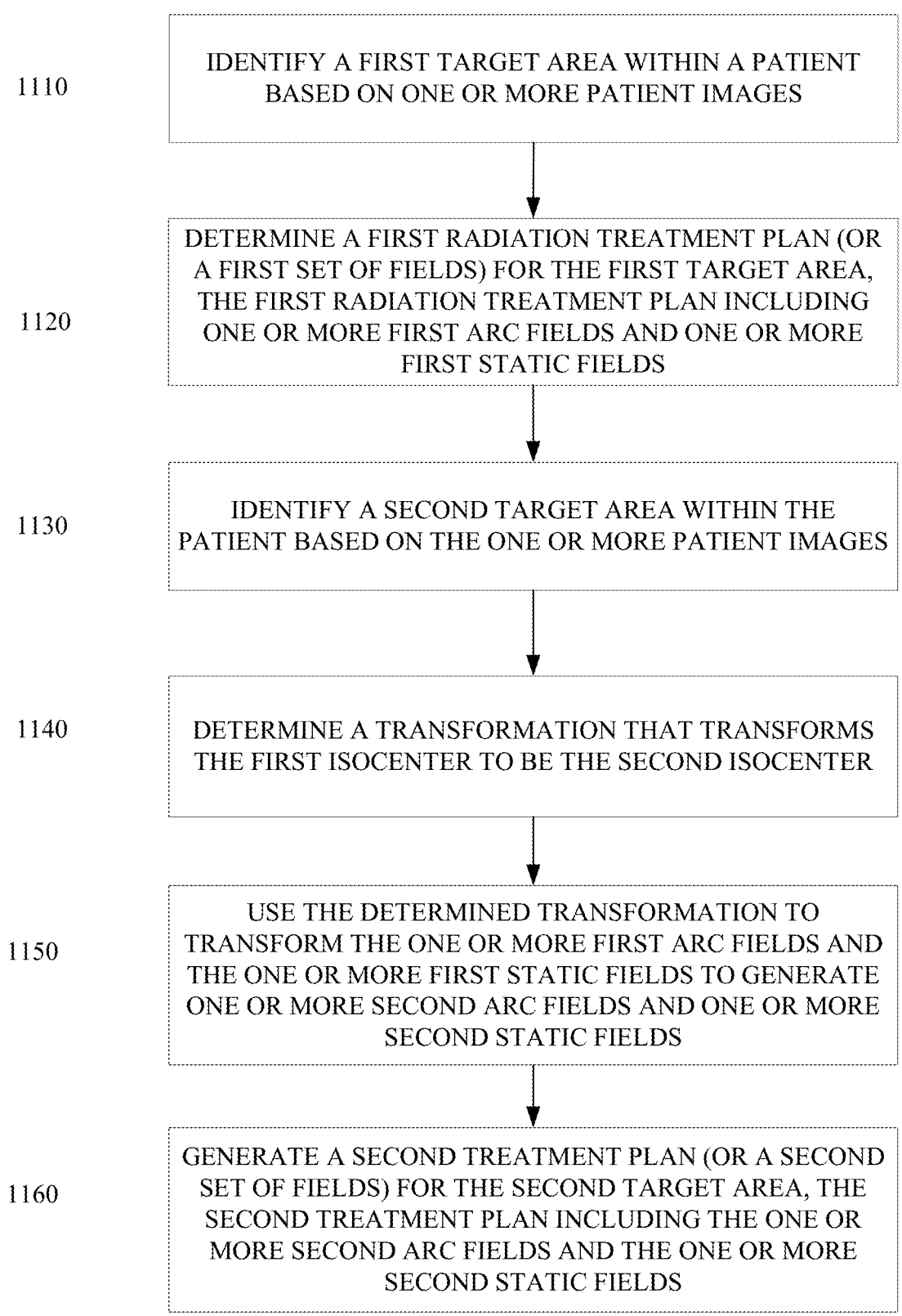
FIG. 11 shows a method for copying a treatment plan from a first target area to a second target area, according to embodiments of the present invention.

FIG. 11 shows a method for copying a treatment plan (or template) from a first target area to a second target area.

At step 1110, a user or radiation treatment system may identify a first target area within the patient. The first target area may be identified based on one or more images associated with the patient. The user or radiation treatment system may also determine a first isocenter location for the first target area.

Further, a first orientation vector may be assigned to the first isocenter. For example, a treatment template may be applied to the target area and centered at the first isocenter. The isocenter orientation vector may be used to align the treatment template (e.g., one or more template radiation fields) correctly around the first isocenter, such that the first target area can be exposed from certain directions.

At step 1120, the user or radiation treatment system may determine a first radiation treatment plan for the first target area. The treatment plan may include one or more arc fields (e.g., with arc field pathways) and one or more static fields (e.g., with one or more static field positions). The treatment plan not need a combination of field types, as there may be any suitable number of fields of any suitable type. In some embodiments, the treatment plan may be determined based on a template, which may be fine-tuned as described above.

At step 1130, the user or radiation treatment system may identify a second target area within the patient. The second target area may also be identified based on one or more images associated with the patient. The user or radiation treatment system may also determine a second isocenter location for the second target area.

Further, a second orientation vector may be assigned to the second isocenter. For example, a treatment template may be applied to the target area and centered at the first isocenter. The isocenter orientation vector may be used to align the treatment template (e.g., one or more template radiation fields) correctly around the first isocenter, such that the first target area can be exposed from certain directions.

At step 1140, the user or radiation treatment system may determine a transformation that transforms the first isocenter to be the second isocenter. For example, one or more mathematical operations may be used to move from the first isocenter position to the second isocenter position. The transformation can include, for example, a rotation, a translation, and a scaling.

As an example of determining a translation, the user or radiation treatment system may determine that the second isocenter is located 10 cm above, 5 cm to the right, and 2 cm behind the first isocenter. As an example of determining a rotation, the user or radiation treatment system may determine that the second isocenter (e.g., or the second orientation vector) is rotated by a certain angle relative to the first isocenter (e.g., or the first orientation vector). There may be up a rotation value for each of the three axis of rotation. As an example of determining a scaling, the user or radiation treatment system may determine that the second isocenter (e.g., or the second target area) is larger or smaller than the first isocenter (e.g., or the first target area) by a certain amount.

In other embodiments, the transformation can be measured as a mirroring. For example, a bisecting line may be placed in between the two isocenters (or in the middle of a certain patient area), and the second isocenter may be copied to an equal and opposite side of the bisecting line relative to the first isocenter.

At step 1150, the user or radiation treatment system may use the determined transformation to transform the treatment plan associated with the first isocenter. For example, the arc fields (and arc field pathways) and static fields (and static field positions) of the treatment plan may be rotated, scaled, and/or translated in the same manner as the second isocenter relative to the first isocenter, thereby obtaining a second set of fields.

At step 1160, the user or radiation treatment system may generate a second treatment plan for the second target area. The treatment plan may include the transformed set of fields from step 1150. The treatment plan for the first isocenter may thereby be copied over to the second isocenter so that the second target area can be similarly irradiated.

Having obtained a treatment plan for the second target area, the treatment plan can then be used to control a radiation treatment system to apply radiation to the patient. In some embodiments, the second treatment plan may be used as a template, and the static fields can be fine-tuned as described above. Further, doses may be calculated and modulation parameters optimized before applying radiation.

VII. Computer System

Figure 12:
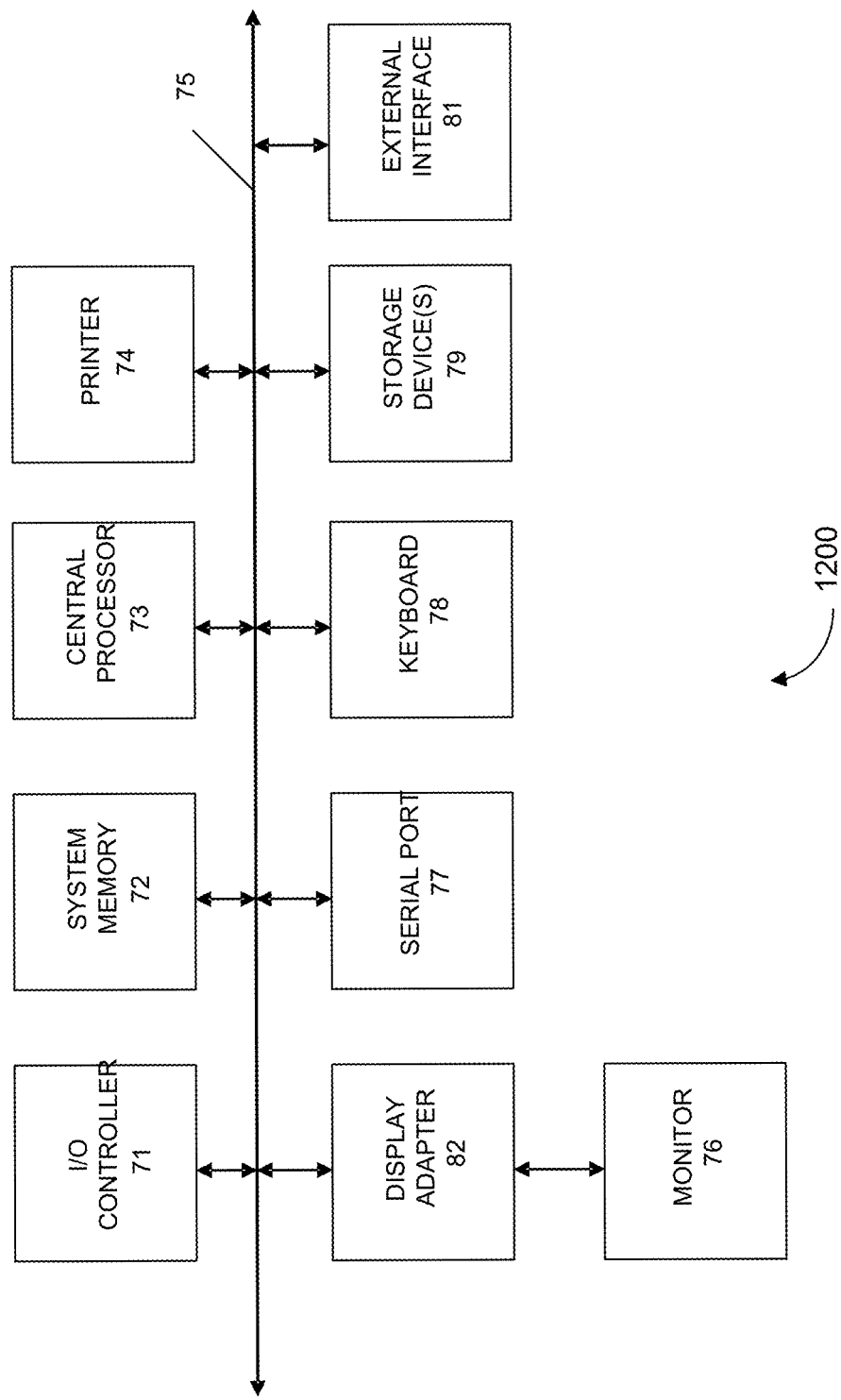
FIG. 12 shows a block diagram of an example computer system usable with system and methods according to embodiments of the present invention.

Any of the computer systems mentioned herein may utilize any suitable number of subsystems. Examples of such subsystems are shown in FIG. 12 in computer apparatus 1200. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 12 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive or optical disk), as well as the exchange of information between subsystems. The system memory 72 and/or the storage device(s) 79 may embody a computer readable medium. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C# or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary. The use of "or" is intended to mean an "inclusive or," and not an "exclusive or" unless specifically indicated to the contrary.

All patents, patent applications, publications, and descriptions mentioned here are incorporated by reference in their entirety for all purposes. None is admitted to be prior art.

What is claimed is:

1. A method for determining a radiation treatment plan for controlling a radiation treatment system to provide radiation to a patient, the method comprising performing by a computer system:
   receiving one or more images associated with the patient;
   identifying a target area within the patient based on the one or more images;
   receiving a selection of a radiation treatment template, wherein the radiation treatment template includes:
      an arc field with an arc field pathway such that the radiation treatment system provides radiation to the target area while a gantry of the radiation treatment system is moving along the arc field pathway, and
      a static field such that the radiation treatment system provides radiation to the target area while the gantry is stationary, the static field having a position at an initial position value;
   obtaining a cost function that outputs a quality score that varies with position values of the static field;
   optimizing the position of the static field by changing the position of the static field and identifying an optimal position value having an optimal quality score, wherein the position of the static field is constrained to be located within a predefined distance of the initial position value; and
   generating a radiation treatment plan using the arc field with the arc field pathway and the static field having the optimal position value, the radiation treatment plan including specifications for providing radiation with the radiation treatment system to the patient over time, along the arc field pathway and at the optimal position value.

2. The method of claim 1, wherein obtaining a cost function includes:
   determining a dose distribution based on the initial position value of the static field, the dose distribution including different doses associated with different locations inside the patient;
   determining a dose gradient based on the dose distribution, the dose gradient including a vector associated with each location inside the patient, each vector indicating a direction of change for the position of the static field that causes the greatest increase in dose at the associated location; and
   determining one or more quality index functions associated with one or more volumes based on the dose gradient, each quality index function providing a vector indicating a direction of change for the position of the static field that causes the greatest increase in a mean dose at the associated volume, wherein the cost function includes the one or more quality index functions that change based on the dose gradient.

3. The method of claim 2, wherein the one or more volumes include a first volume associated with the target area and a second volume associated with a healthy organ.

4. The method of claim 3, wherein the quality score is improved when a mean dose associated with the target area is increased and when a mean dose associated with the healthy organ is decreased.

5. The method of claim 4, wherein the cost function includes a first term associated with the mean dose for the target area, the first term including a minimum mean dose value, and wherein the cost function includes a second term associated with the mean dose for the healthy organ, the second term including a maximum mean dose value.

6. The method of claim 5, wherein the quality score is improved when the mean dose for the target area exceeds the minimum mean dose value, wherein the quality score is penalized when the mean dose for the target area is less than the minimum mean dose value, a first penalization amount increasing as the mean dose for the target area is reduced, wherein the quality score is improved when the mean dose for the healthy organ is less than the maximum mean dose value, and wherein the quality score is penalized when the mean dose for the healthy organ exceeds the maximum mean dose value, a second penalization amount increasing as the mean dose for the healthy organ increases.

7. The method of claim 6, wherein the cost function includes a first weight specifying a magnitude with which the first penalization amount affects the quality score, and wherein the cost function includes a second weight specifying a magnitude with which the second penalization amount affects the quality score.

8. The method of claim 1, wherein the position of the static field includes a gantry position, a treatment bed position, and a collimator position.

9. The method of claim 8, wherein the dose gradient includes a partial derivative of the dose distribution with respect to gantry position, a partial derivative of the dose distribution with respect to treatment bed position, and a partial derivative of the dose distribution with respect to collimator position.

10. The method of claim 1, wherein the target area includes a tumor.

11. The method of claim 1, wherein the static field is a first static field, and wherein the radiation treatment template further includes:
   a second static field such that the radiation treatment system provides radiation to the target area while the gantry is stationary, the second static field having a position at a second initial position value,
   wherein the cost function quality score varies with position values of both the first static field and the second static field, the method further comprising:
   optimizing the position of the first static field together with the position of the second static field by identifying a first optimal position value for the first static field and a second optimal position value for the second static field, the first optimal position value and the second optimal position value having an optimal quality score, wherein the position of the second static field is constrained to be located within a second predefined distance of the second initial position value.

12. The method of claim 1, wherein the arc field pathway of the arc field is not optimized for the radiation treatment plan.

13. The method of claim 1, further comprising:
   providing the radiation treatment plan to a control system of the radiation treatment system; and
   controlling, by the control system, one or more components of the radiation treatment system to provide radiation to the patient according to the specifications of the radiation treatment plan.

14. The method of claim 1, wherein the radiation treatment template is selected based on a location of the target area.

15. The method of claim 1, wherein the target area is a first target area having a first isocenter within the patient, the method further comprising:
   identifying a second target area within the patient based on the one or more images, the second target area having a second isocenter within the patient;

determining a transformation that transforms the first isocenter to be the second isocenter;

using the transformation to transform the arc field and the static field to generate a second arc field with a second arc field pathway and a second static field having a second position; and generating a second radiation treatment plan using the second arc field and the second static field, the second radiation treatment plan including specifications for providing radiation with the radiation treatment system to the patient over time, along the second arc field pathway and at the second position.

16. A method for determining a radiation treatment plan, the method comprising:

receiving one or more images associated with a patient;

identifying a first target area within the patient based on the one or more images, the first target area having a first isocenter within the patient;

determining, at a computer, one or more first fields such that a radiation treatment system provides radiation to the first target area, identifying a second target area within the patient based on the one or more images, the second target area having a second isocenter within the patient;

determining a transformation that transforms the first isocenter to be the second isocenter;

using the transformation to transform the one or more first fields to generate one or more second fields; and generating a treatment plan using the one or more first fields and the one or more second fields, the radiation treatment plan including specifications for providing radiation with the radiation treatment system to the patient over time according to the one or more first fields and the one or more second fields.

17. The method of claim 16, wherein the one or more first fields include:

a first arc field with a first arc field pathway such that the radiation treatment system provides radiation to the first target area while a gantry of the radiation treatment system is moving along the first arc field pathway, and a first static field having a first position such that the radiation treatment system provides radiation to the first target area while the gantry is stationary, wherein the one or more second fields include:

a second arc field with a second arc field pathway, and a second static field having a second position, and wherein the radiation treatment plan specifications include providing radiation with the radiation treatment system to the patient over time along the first arc field pathway and at the first position and along the second arc field pathway and at the second position.

18. The method of claim 17, wherein the transformation includes at least one of a rotation, a translation, and a scaling.

19. The method of claim 18, wherein the first isocenter is associated with a first location, wherein the second isocenter is associated with a second location, wherein the first position of the first static field includes a third location, wherein the second position of the second static field includes a fourth location, wherein a translation transforms the first location into the second location, and wherein the translation is used to translate the third location into the fourth location.

20. The method of claim 17, wherein the transformation includes mirroring the first static field and the second arc field across a bisecting line located midway between the first isocenter and the second isocenter.

* * * * *